US010448992B2

(12) United States Patent
Cadouri et al.

(10) Patent No.: US 10,448,992 B2
(45) Date of Patent: Oct. 22, 2019

(54) ELECTROSURGICAL SYSTEM WITH DEVICE SPECIFIC OPERATIONAL PARAMETERS

(75) Inventors: Hadar Cadouri, Sunnyvale, CA (US); Jean Woloszko, Austin, TX (US); Philip M. Tetzlaff, Austin, TX (US)

(73) Assignee: ArthroCare Corporation, Austin, TX (US)

( * ) Notice: Subject to any disclaimer, the term of this patent is extended or adjusted under 35 U.S.C. 154(b) by 1642 days.

(21) Appl. No.: 12/909,930

(22) Filed: Oct. 22, 2010

(65) Prior Publication Data

US 2012/0101494 A1  Apr. 26, 2012

(51) Int. Cl.
*A61B 18/14* (2006.01)
*A61B 18/16* (2006.01)

(52) U.S. Cl.
CPC ............ *A61B 18/148* (2013.01); *A61B 18/16* (2013.01); *A61B 2217/007* (2013.01); *A61B 2218/002* (2013.01)

(58) Field of Classification Search
CPC ........ A61B 18/148; A61B 2018/00583; A61B 2018/00625
USPC ....................................................... 606/34, 38
See application file for complete search history.

(56) References Cited

U.S. PATENT DOCUMENTS

| 2,050,904 A | 8/1936 | Talley ............................ 219/233 |
| 2,056,377 A | 10/1939 | Wappler ......................... 125/303 |
| 3,633,425 A | 1/1972 | Sanford .......................... 73/356 |
| 3,815,604 A | 6/1974 | O'Malley et al. ............. 128/305 |
| 3,828,780 A | 8/1974 | Morrison, Jr. et al. ........ 128/275 |
| 3,901,242 A | 8/1975 | Storz ............................... 128/303 |
| 3,920,021 A | 11/1975 | Hiltebrandt .................... 128/303 |
| 3,939,839 A | 2/1976 | Curtiss ........................... 128/303 |
| 3,970,088 A | 7/1976 | Morrison ....................... 128/303 |
| 4,033,351 A | 7/1977 | Hetzel ............................. 606/48 |
| 4,040,426 A | 8/1977 | Morrison, Jr. ................. 128/303 |

(Continued)

FOREIGN PATENT DOCUMENTS

| DE | 3930451 A1 | 3/1991 | ............. A61B 17/39 |
| EP | 0703461 A2 | 3/1996 | ............. G01B 27/02 |

(Continued)

OTHER PUBLICATIONS

Barry et al., "The Effect of Radiofrequency-generated Thermal Energy on the Mechanical and Histologic Characteristics of the Arterial Wall in Vivo: Implications of Radiofrequency Angioplasty" *American Heart Journal* vol. 117, pp. 332-341, 1982.

(Continued)

*Primary Examiner* — Linda C Dvorak
*Assistant Examiner* — Ryan T Clark
(74) *Attorney, Agent, or Firm* — Mark J. Gorman

(57) ABSTRACT

Electrosurgical systems and methods include a generator which is operable to connect to an electrosurgical device and to identify the electrosurgical device. The generator automatically determines at least one device specific operational parameter for carrying out the electrosurgical procedure. In an exemplary embodiment, a generator includes a fluid pump and the generator automatically determines a candidate flowrate at which to operate the pump based on the type of device. The device specific operational parameter may be selected or modified by the operator prior to commencing the procedure.

29 Claims, 8 Drawing Sheets

(56) References Cited

U.S. PATENT DOCUMENTS

| | | | | |
|---|---|---|---|---|
| 4,043,342 A | 8/1977 | Morrison, Jr. | | 128/303 |
| 4,074,718 A | 2/1978 | Morrison, Jr. | | 128/303 |
| 4,092,986 A | 6/1978 | Schneiderman | | 128/303 |
| 4,116,198 A | 9/1978 | Roos | | 128/303 |
| 4,181,131 A | 1/1980 | Ogiu | | 128/303 |
| 4,184,492 A | 1/1980 | Meinke et al. | | 128/303 |
| 4,202,337 A | 5/1980 | Hren et al. | | 128/303 |
| 4,228,800 A | 10/1980 | Degler, Jr. et al. | | 128/303 |
| 4,232,676 A | 11/1980 | Herczog | | 128/303 |
| 4,248,231 A | 2/1981 | Herczog et al. | | 128/303 |
| 4,301,802 A | 11/1981 | Poler | | 606/48 |
| 4,326,529 A | 4/1982 | Doss et al. | | 128/303 |
| 4,381,007 A | 4/1983 | Doss | | 128/303 |
| 4,474,179 A | 10/1984 | Koch | | 606/40 |
| 4,476,862 A | 10/1984 | Pao | | 128/303 |
| 4,532,924 A | 8/1985 | Auth et al. | | 128/303 |
| 4,548,207 A | 10/1985 | Reimels | | 128/303 |
| 4,567,890 A | 2/1986 | Ohta et al. | | 128/303 |
| 4,582,057 A | 4/1986 | Auth et al. | | 606/31 |
| 4,590,934 A | 5/1986 | Malis et al. | | 128/303 |
| 4,593,691 A | 6/1986 | Lindstrom et al. | | 128/303 |
| 4,658,817 A | 4/1987 | Hardy | | 606/14 |
| 4,660,571 A | 4/1987 | Hess et al. | | 128/784 |
| 4,674,499 A | 6/1987 | Pao | | 128/303 |
| 4,682,596 A | 7/1987 | Bales et al. | | 128/303 |
| 4,706,667 A | 11/1987 | Roos | | 128/303 |
| 4,709,698 A | 12/1987 | Johnston et al. | | 606/41 |
| 4,727,874 A | 3/1988 | Bowers et al. | | 128/303 |
| 4,765,331 A | 8/1988 | Petruzzi et al. | | 128/303 |
| 4,785,823 A | 11/1988 | Eggers et al. | | 128/692 |
| 4,805,616 A | 2/1989 | Pao | | 128/303 |
| 4,823,791 A | 4/1989 | D'Amelio et al. | | 123/303 |
| 4,832,048 A | 5/1989 | Cohen | | 128/786 |
| 4,860,752 A | 8/1989 | Turner | | 607/102 |
| 4,907,589 A | 3/1990 | Cosman | | 606/34 |
| 4,920,978 A | 5/1990 | Colvin | | 128/784 |
| 4,931,047 A | 6/1990 | Broadwin et al. | | 604/22 |
| 4,936,281 A | 6/1990 | Stasz | | 128/660 |
| 4,936,301 A | 6/1990 | Rexroth et al. | | 606/45 |
| 4,943,290 A | 7/1990 | Rexroth et al. | | 606/45 |
| 4,966,597 A | 10/1990 | Cosman | | 606/50 |
| 4,967,765 A | 11/1990 | Turner et al. | | 128/785 |
| 4,976,711 A | 12/1990 | Parins et al. | | 606/48 |
| 4,979,948 A | 12/1990 | Geddes et al. | | 606/33 |
| 4,998,933 A | 3/1991 | Eggers et al. | | 606/41 |
| 5,007,908 A | 4/1991 | Rydell | | 606/47 |
| 5,009,656 A | 4/1991 | Reimels | | 606/48 |
| 5,035,696 A | 7/1991 | Rydell | | 606/47 |
| 5,047,026 A | 9/1991 | Rydell | | 606/48 |
| 5,047,027 A | 9/1991 | Rydell | | 606/48 |
| 5,057,105 A | 10/1991 | Malone et al. | | 606/28 |
| 5,057,106 A | 10/1991 | Kasevich et al. | | 606/33 |
| 5,078,716 A | 1/1992 | Doll | | 606/47 |
| 5,078,717 A | 1/1992 | Parins et al. | | 606/48 |
| 5,080,660 A | 1/1992 | Buelna | | 606/45 |
| 5,083,565 A | 1/1992 | Parins | | 600/374 |
| 5,084,044 A | 1/1992 | Quint | | 606/27 |
| 5,085,659 A | 2/1992 | Rydell | | 606/47 |
| 5,088,997 A | 2/1992 | Delahuerga et al. | | 606/42 |
| 5,098,431 A | 3/1992 | Rydell | | 606/48 |
| 5,099,840 A | 3/1992 | Goble | | 128/422 |
| 5,102,410 A | 4/1992 | Dressel | | 606/15 |
| 5,108,391 A | 4/1992 | Flachenecker et al. | | 606/38 |
| RE33,925 E | 5/1992 | Bales et al. | | 606/48 |
| 5,112,330 A | 5/1992 | Nishigaki et al. | | 606/46 |
| 5,122,138 A | 6/1992 | Manwaring | | 606/46 |
| 5,125,928 A | 6/1992 | Parins et al. | | 606/48 |
| 5,156,151 A | 10/1992 | Imran | | 600/375 |
| 5,167,659 A | 12/1992 | Ohtomo et al. | | 606/40 |
| 5,167,660 A | 12/1992 | Altendorf | | 606/40 |
| 5,171,311 A | 12/1992 | Rydell et al. | | 606/48 |
| 5,178,620 A | 1/1993 | Eggers et al. | | 606/41 |
| 5,190,517 A | 3/1993 | Zieve et al. | | 604/22 |
| 5,192,280 A | 3/1993 | Parins | | 606/48 |
| 5,195,959 A | 3/1993 | Smith | | 604/34 |
| 5,195,968 A | 3/1993 | Lundquist et al. | | 604/95.04 |
| 5,196,007 A | 3/1993 | Ellman | | 606/32 |
| 5,197,466 A | 3/1993 | Marchosky et al. | | 128/399 |
| 5,197,963 A | 3/1993 | Parins | | 606/46 |
| 5,207,675 A | 5/1993 | Canady | | 606/40 |
| 5,217,457 A | 6/1993 | Delahuerga et al. | | 606/42 |
| 5,217,459 A | 6/1993 | Kamerling | | 606/48 |
| 5,249,585 A | 10/1993 | Turner et al. | | 607/99 |
| 5,261,410 A | 11/1993 | Alfano et al. | | 600/475 |
| 5,267,994 A | 12/1993 | Gentelia et al. | | 606/15 |
| 5,267,997 A | 12/1993 | Farin et al. | | 606/38 |
| 5,273,524 A | 12/1993 | Fox et al. | | 604/21 |
| 5,277,201 A | 1/1994 | Stern | | 607/98 |
| 5,281,216 A | 1/1994 | Klicek | | 606/42 |
| 5,281,218 A | 1/1994 | Imran | | 606/41 |
| 5,290,282 A | 3/1994 | Casscells | | 606/29 |
| 5,300,069 A | 4/1994 | Hunsberger et al. | | 606/37 |
| 5,306,238 A | 4/1994 | Fleenor | | 606/42 |
| 5,312,400 A | 5/1994 | Bales et al. | | 606/41 |
| 5,314,406 A | 5/1994 | Arias et al. | | 604/21 |
| 5,324,254 A | 6/1994 | Phillips | | 604/21 |
| 5,330,470 A | 7/1994 | Hagen | | 606/42 |
| 5,334,140 A | 8/1994 | Philips | | 604/35 |
| 5,334,183 A | 8/1994 | Wuchinich | | 606/46 |
| 5,334,193 A | 8/1994 | Nardella | | 606/41 |
| 5,336,220 A | 8/1994 | Ryan et al. | | 604/22 |
| 5,336,443 A | 8/1994 | Eggers | | 252/511 |
| 5,342,357 A | 8/1994 | Nardella | | 606/40 |
| 5,363,861 A | 11/1994 | Edwards et al. | | 600/585 |
| 5,366,443 A | 11/1994 | Eggers et al. | | 604/114 |
| 5,370,675 A | 12/1994 | Edwards et al. | | 607/101 |
| 5,374,261 A | 12/1994 | Yoon | | 604/385.01 |
| 5,375,588 A | 12/1994 | Yoon | | 128/4 |
| 5,380,277 A | 1/1995 | Phillips | | 604/33 |
| 5,380,316 A | 1/1995 | Aita | | 606/7 |
| 5,383,876 A | 1/1995 | Nardella | | 606/49 |
| 5,383,917 A | 1/1995 | Desai et al. | | 607/702 |
| 5,389,096 A | 2/1995 | Aita | | 606/15 |
| 5,395,312 A | 3/1995 | Desai | | 604/22 |
| 5,395,363 A | 3/1995 | Billings et al. | | 606/41 |
| 5,395,368 A | 3/1995 | Ellman et al. | | 606/45 |
| 5,400,267 A | 3/1995 | Denen et al. | | 702/59 |
| 5,401,272 A | 3/1995 | Perkins | | 606/15 |
| 5,403,311 A | 4/1995 | Abele et al. | | 606/49 |
| 5,417,687 A | 5/1995 | Nardella et al. | | 606/32 |
| 5,419,767 A | 5/1995 | Eggers et al. | | 604/114 |
| 5,423,810 A | 6/1995 | Goble et al. | | 606/40 |
| 5,423,811 A | 6/1995 | Imran et al. | | 606/41 |
| 5,423,812 A | 6/1995 | Ellman et al. | | 606/45 |
| 5,423,882 A | 6/1995 | Jackman et al. | | 607/122 |
| 5,436,566 A | 7/1995 | Thompson et al. | | 324/713 |
| 5,437,662 A | 8/1995 | Nardella | | 606/40 |
| 5,438,302 A | 8/1995 | Goble | | 331/167 |
| 5,441,499 A | 8/1995 | Fritzsch | | 606/45 |
| 5,451,224 A | 9/1995 | Goble et al. | | 606/48 |
| 5,454,809 A | 10/1995 | Janssen | | 606/41 |
| 5,456,662 A | 10/1995 | Edwards et al. | | 604/22 |
| 5,458,596 A | 10/1995 | Lax et al. | | 606/31 |
| 5,487,757 A | 1/1996 | Truckai et al. | | 604/264 |
| 5,490,850 A | 2/1996 | Ellman et al. | | 606/45 |
| 5,496,312 A | 3/1996 | Klicek | | 606/34 |
| 5,496,314 A | 3/1996 | Eggers | | 606/41 |
| 5,496,317 A | 3/1996 | Goble et al. | | 606/48 |
| 5,505,728 A | 4/1996 | Ellman et al. | | 606/39 |
| 5,505,730 A | 4/1996 | Edwards | | 606/41 |
| 5,514,130 A | 5/1996 | Baker | | 606/41 |
| 5,554,152 A | 9/1996 | Aita | | 606/7 |
| 5,556,397 A | 9/1996 | Long et al. | | 606/48 |
| 5,562,503 A | 10/1996 | Ellman et al. | | 439/638 |
| 5,562,703 A | 10/1996 | Desai | | 606/210 |
| 5,569,242 A | 10/1996 | Lax et al. | | 606/42 |
| 5,571,100 A | 11/1996 | Goble et al. | | 606/41 |
| 5,571,101 A | 11/1996 | Ellman et al. | | 606/45 |
| 5,584,872 A | 12/1996 | LaFontaine et al. | | 607/117 |
| 5,609,151 A | 3/1997 | Mulier et al. | | 128/642 |
| 5,624,439 A | 4/1997 | Edwards et al. | | 606/45 |
| 5,630,812 A | 5/1997 | Ellman et al. | | 606/41 |
| 5,633,578 A | 5/1997 | Eggers et al. | | 323/301 |
| 5,636,861 A | 6/1997 | Orsulak et al. | | 600/585 |

(56) References Cited

U.S. PATENT DOCUMENTS

| | | | |
|---|---|---|---|
| 5,647,869 A | 7/1997 | Goble et al. | 606/37 |
| 5,658,278 A | 8/1997 | Imran et al. | 606/41 |
| 5,662,680 A | 9/1997 | Desai | 606/210 |
| 5,674,191 A | 10/1997 | Edwards et al. | 604/22 |
| 5,676,693 A | 10/1997 | LaFontaine et al. | 607/116 |
| 5,681,282 A | 10/1997 | Eggers et al. | 604/114 |
| 5,683,366 A | 11/1997 | Eggers et al. | 604/114 |
| 5,683,386 A | 11/1997 | Ellman et al. | 606/41 |
| 5,683,387 A | 11/1997 | Garito et al. | 606/45 |
| 5,688,267 A | 11/1997 | Panescu et al. | 606/41 |
| 5,695,495 A | 12/1997 | Ellman et al. | 606/41 |
| 5,697,281 A | 12/1997 | Eggers et al. | 604/114 |
| 5,697,536 A | 12/1997 | Eggers et al. | 604/114 |
| 5,697,882 A | 12/1997 | Eggers et al. | 604/114 |
| 5,697,909 A | 12/1997 | Eggers et al. | 604/114 |
| 5,700,262 A | 12/1997 | Acosta et al. | 606/48 |
| 5,707,349 A | 1/1998 | Edwards | 604/22 |
| 5,718,702 A | 2/1998 | Edwards | 606/41 |
| 5,725,524 A | 3/1998 | Mulier et al. | 606/41 |
| 5,728,094 A | 3/1998 | Edwards | 606/41 |
| 5,733,282 A | 3/1998 | Ellman et al. | 606/45 |
| 5,738,114 A | 4/1998 | Edwards | 128/898 |
| 5,743,870 A | 4/1998 | Edwards | 604/22 |
| 5,746,224 A | 5/1998 | Edwards | 128/898 |
| 5,749,869 A | 5/1998 | Lindenmeier et al. | 606/34 |
| 5,766,153 A | 6/1998 | Eggers et al. | 604/114 |
| 5,775,338 A | 7/1998 | Hastings | 128/898 |
| 5,776,128 A | 7/1998 | Eggers | 606/48 |
| 5,782,828 A | 7/1998 | Chen et al. | 606/42 |
| 5,800,379 A | 9/1998 | Edwards | 604/22 |
| 5,800,429 A | 9/1998 | Edwards | 606/41 |
| 5,807,395 A | 9/1998 | Mulier et al. | 606/41 |
| 5,810,764 A | 9/1998 | Eggers et al. | 604/23 |
| 5,810,809 A | 9/1998 | Rydell | 606/49 |
| 5,817,049 A | 10/1998 | Edwards | 604/22 |
| 5,820,580 A | 10/1998 | Edwards et al. | 604/22 |
| 5,823,197 A | 10/1998 | Edwards | 128/898 |
| 5,827,277 A | 10/1998 | Edwards | 606/41 |
| 5,836,875 A | 11/1998 | Webster, Jr. | 600/374 |
| 5,843,019 A | 12/1998 | Eggers et al. | 604/22 |
| 5,843,021 A | 12/1998 | Edwards et al. | 604/22 |
| 5,843,077 A | 12/1998 | Edwards | 606/41 |
| 5,860,951 A | 1/1999 | Eggers | 604/510 |
| 5,860,974 A | 1/1999 | Abele | 606/41 |
| 5,860,975 A | 1/1999 | Goble et al. | 606/41 |
| 5,871,469 A | 2/1999 | Eggers et al. | 604/114 |
| 5,873,855 A | 2/1999 | Eggers et al. | 604/114 |
| 5,879,349 A | 3/1999 | Edwards | 606/45 |
| 5,885,277 A | 3/1999 | Korth | 606/35 |
| 5,888,198 A | 3/1999 | Eggers et al. | 604/114 |
| 5,891,095 A | 4/1999 | Eggers et al. | 604/114 |
| 5,891,134 A | 4/1999 | Goble et al. | 606/27 |
| 5,897,553 A | 4/1999 | Mulier | 606/41 |
| 5,902,272 A | 5/1999 | Eggers et al. | 604/114 |
| 5,916,214 A | 6/1999 | Cosio et al. | 606/41 |
| 5,919,190 A | 7/1999 | Vandusseldorp | 606/46 |
| 5,921,983 A | 7/1999 | Shannon, Jr. | 606/45 |
| 5,944,715 A | 8/1999 | Goble et al. | 606/41 |
| 5,954,716 A | 9/1999 | Sharkey et al. | 606/32 |
| 5,988,171 A | 11/1999 | Sohn et al. | 128/848 |
| 6,004,319 A | 12/1999 | Goble et al. | 606/48 |
| 6,006,755 A | 12/1999 | Edwards | 128/898 |
| 6,009,877 A | 1/2000 | Edwards | 128/898 |
| 6,013,076 A | 1/2000 | Goble et al. | 606/41 |
| 6,015,406 A | 1/2000 | Goble et al. | 606/41 |
| 6,024,733 A | 2/2000 | Eggers et al. | 604/500 |
| 6,026,816 A | 2/2000 | McMillan et al. | 128/898 |
| 6,027,501 A | 2/2000 | Goble et al. | 606/41 |
| 6,039,734 A | 3/2000 | Goble et al. | 606/41 |
| 6,044,846 A | 4/2000 | Edwards | 128/898 |
| 6,047,700 A | 4/2000 | Eggers et al. | 128/898 |
| 6,056,746 A | 5/2000 | Goble et al. | 606/48 |
| 6,063,079 A | 5/2000 | Hovda et al. | 606/41 |
| 6,066,134 A | 5/2000 | Eggers et al. | 606/32 |
| 6,066,139 A | 5/2000 | Ryan et al. | 606/50 |
| 6,068,628 A | 5/2000 | Fanton et al. | 606/41 |
| 6,071,281 A | 6/2000 | Burnside et al. | 606/41 |
| 6,073,052 A | 6/2000 | Zelickson et al. | 607/100 |
| 6,074,386 A | 6/2000 | Goble et al. | 606/34 |
| 6,086,585 A | 7/2000 | Hovda et al. | 606/45 |
| 6,090,106 A | 7/2000 | Goble et al. | 606/41 |
| 6,093,186 A | 7/2000 | Goble et al. | 606/34 |
| 6,102,046 A | 8/2000 | Weinstein et al. | 128/898 |
| 6,105,581 A | 8/2000 | Eggers et al. | 128/898 |
| 6,109,268 A | 8/2000 | Thapliyal et al. | 128/898 |
| 6,117,109 A | 9/2000 | Eggers et al. | 604/114 |
| 6,126,682 A | 10/2000 | Sharkey et al. | 607/96 |
| 6,142,992 A | 11/2000 | Cheng et al. | 606/34 |
| 6,149,620 A | 11/2000 | Baker et al. | 604/22 |
| 6,159,194 A | 12/2000 | Eggers et al. | 604/500 |
| 6,159,208 A | 12/2000 | Hovda et al. | 606/41 |
| 6,168,593 B1 | 1/2001 | Sharkey et al. | 606/34 |
| 6,174,309 B1 | 1/2001 | Wrublewski et al. | 606/45 |
| 6,179,824 B1 | 1/2001 | Eggers et al. | 604/500 |
| 6,179,836 B1 | 1/2001 | Eggers et al. | 606/45 |
| 6,183,469 B1 | 2/2001 | Thapliyal et al. | 606/41 |
| 6,190,381 B1 | 2/2001 | Olsen et al. | 606/32 |
| 6,203,542 B1 | 3/2001 | Ellsberry et al. | 606/41 |
| 6,210,402 B1 | 4/2001 | Olsen et al. | 606/32 |
| 6,210,405 B1 | 4/2001 | Goble et al. | 606/41 |
| 6,224,592 B1 | 5/2001 | Eggers et al. | 606/32 |
| 6,228,078 B1 | 5/2001 | Eggers | 606/32 |
| 6,228,081 B1 | 5/2001 | Goble | 606/34 |
| 6,234,178 B1 | 5/2001 | Eggers | 606/32 |
| 6,235,020 B1 | 5/2001 | Cheng et al. | 606/34 |
| 6,237,604 B1 | 5/2001 | Burnside et al. | 128/897 |
| 6,238,391 B1 | 5/2001 | Olsen et al. | 606/41 |
| 6,254,600 B1 | 7/2001 | Willink et al. | 606/41 |
| 6,258,086 B1 | 7/2001 | Ashley et al. | 606/41 |
| 6,261,286 B1 | 7/2001 | Goble et al. | 606/34 |
| 6,261,311 B1 | 7/2001 | Sharkey et al. | 607/96 |
| 6,264,652 B1 | 7/2001 | Eggers et al. | 606/41 |
| 6,270,460 B1 | 8/2001 | McCartan et al. | 600/459 |
| 6,270,476 B1 | 8/2001 | Santoianni et al. | 604/95.04 |
| 6,277,112 B1 | 8/2001 | Underwood et al. | 606/32 |
| 6,280,441 B1 | 8/2001 | Ryan | 606/45 |
| 6,283,961 B1 | 9/2001 | Underwood et al. | 606/41 |
| 6,293,942 B1 | 9/2001 | Goble et al. | 606/38 |
| 6,296,636 B1 | 10/2001 | Cheng et al. | 606/32 |
| 6,296,638 B1 | 10/2001 | Davison et al. | 606/41 |
| 6,306,134 B1 | 10/2001 | Goble et al. | 606/42 |
| 6,308,089 B1 | 10/2001 | von der Rur et al. | 600/338 |
| 6,309,387 B1 | 10/2001 | Eggers et al. | 606/41 |
| 6,312,408 B1 | 11/2001 | Eggers et al. | 604/114 |
| 6,322,549 B1 | 11/2001 | Eggers et al. | 604/500 |
| 6,355,032 B1 | 3/2002 | Hovda et al. | 606/32 |
| 6,363,937 B1 | 4/2002 | Hovda et al. | 128/898 |
| 6,364,877 B1 | 4/2002 | Goble et al. | 606/34 |
| 6,379,350 B1 | 4/2002 | Sharkey et al. | 606/41 |
| 6,379,351 B1 | 4/2002 | Thapliyal et al. | 606/41 |
| 6,387,093 B1 | 5/2002 | Ellman et al. | 606/39 |
| 6,391,025 B1 | 5/2002 | Weinstein et al. | 606/41 |
| 6,409,722 B1 * | 6/2002 | Hoey et al. | 606/34 |
| 6,411,852 B1 | 6/2002 | Danek et al. | 607/42 |
| 6,413,254 B1 | 7/2002 | Hissong et al. | 606/27 |
| 6,416,491 B1 | 7/2002 | Edwards et al. | 606/41 |
| 6,416,507 B1 | 7/2002 | Eggers et al. | 606/32 |
| 6,416,508 B1 | 7/2002 | Eggers et al. | 606/32 |
| 6,416,509 B1 | 7/2002 | Goble et al. | 606/37 |
| 6,427,089 B1 | 7/2002 | Knowlton | 607/101 |
| 6,432,103 B1 | 8/2002 | Ellsberry et al. | 606/41 |
| 6,464,689 B1 * | 10/2002 | Qin et al. | 606/1 |
| 6,464,699 B1 | 10/2002 | Swanson | 606/41 |
| 6,468,274 B1 | 10/2002 | Alleyne et al. | 606/32 |
| 6,468,275 B1 | 10/2002 | Wampler et al. | 606/48 |
| 6,482,201 B1 | 11/2002 | Olsen et al. | 606/41 |
| 6,491,690 B1 | 12/2002 | Goble et al. | 606/41 |
| 6,517,498 B1 | 2/2003 | Burbank et al. | 600/564 |
| 6,530,922 B2 | 3/2003 | Cosman | 606/34 |
| 6,530,924 B1 | 3/2003 | Ellman et al. | 606/45 |
| 6,551,032 B1 | 4/2003 | Nolan et al. | 407/13 |
| 6,572,613 B1 | 6/2003 | Ellman et al. | 606/45 |
| 6,578,579 B2 | 6/2003 | Burnside | 128/897 |
| 6,589,235 B2 | 7/2003 | Wong et al. | 606/32 |

(56) References Cited

U.S. PATENT DOCUMENTS

| | | | |
|---|---|---|---|
| 6,589,237 B2 | 7/2003 | Woloszko et al. | 606/41 |
| 6,602,248 B1 | 8/2003 | Sharps et al. | 606/32 |
| 6,620,156 B1 | 9/2003 | Garito et al. | 606/50 |
| 6,632,193 B1 | 10/2003 | Davison et al. | 604/22 |
| 6,632,220 B1 | 10/2003 | Eggers et al. | 606/41 |
| 6,666,860 B1* | 12/2003 | Takahashi | 606/34 |
| 6,746,447 B2 | 6/2004 | Davison et al. | 606/41 |
| 6,749,604 B1 | 6/2004 | Eggers et al. | 606/41 |
| 6,749,608 B2 | 6/2004 | Garito et al. | 606/45 |
| 6,770,071 B2 | 8/2004 | Woloszko et al. | 606/41 |
| 6,780,178 B2 | 8/2004 | Palanker et al. | 600/41 |
| 6,780,180 B1 | 8/2004 | Goble et al. | 606/41 |
| 6,802,842 B2 | 10/2004 | Ellman et al. | 606/45 |
| 6,837,887 B2 | 1/2005 | Woloszko et al. | 606/41 |
| 6,837,888 B2 | 1/2005 | Ciarrocca et al. | 606/41 |
| 6,920,883 B2 | 7/2005 | Bessette et al. | 128/898 |
| 6,929,640 B1 | 8/2005 | Underwood et al. | 606/32 |
| 6,949,096 B2 | 9/2005 | Davison et al. | 606/41 |
| 6,955,172 B2 | 10/2005 | Nelson et al. | 128/848 |
| 6,960,204 B2 | 11/2005 | Eggers et al. | 606/32 |
| 6,974,453 B2 | 12/2005 | Woloszko et al. | 606/41 |
| 6,984,231 B2 | 1/2006 | Goble et al. | 606/37 |
| 6,991,631 B2 | 1/2006 | Woloszko et al. | 606/41 |
| 7,004,941 B2 | 2/2006 | Tvinnereim et al. | 606/41 |
| 7,041,102 B2 | 5/2006 | Truckai et al. | 606/51 |
| 7,070,596 B1 | 7/2006 | Woloszko et al. | 606/41 |
| 7,090,672 B2 | 8/2006 | Underwood et al. | 606/41 |
| 7,094,215 B2 | 8/2006 | Davison et al. | 604/22 |
| 7,104,986 B2 | 9/2006 | Hovda et al. | 606/32 |
| 7,131,969 B1 | 11/2006 | Hovda et al. | 606/45 |
| 7,169,143 B2 | 1/2007 | Eggers et al. | 606/32 |
| 7,179,255 B2 | 2/2007 | Lettice et al. | 606/32 |
| 7,186,234 B2 | 3/2007 | Dahla et al. | 604/22 |
| 7,192,428 B2 | 3/2007 | Eggers et al. | 606/41 |
| 7,201,750 B1 | 4/2007 | Eggers et al. | 606/41 |
| 7,217,268 B2 | 5/2007 | Eggers et al. | 606/41 |
| 7,241,293 B2 | 7/2007 | Davison | 600/410 |
| 7,270,658 B2 | 9/2007 | Woloszko et al. | 606/32 |
| 7,270,659 B2 | 9/2007 | Hovda et al. | 606/32 |
| 7,270,661 B2 | 9/2007 | Dahla et al. | 606/41 |
| 7,276,063 B2 | 10/2007 | Davison et al. | 606/41 |
| 7,297,143 B2 | 11/2007 | Woloszko et al. | 606/41 |
| 7,297,145 B2 | 11/2007 | Ormsby et al. | 606/41 |
| 7,318,823 B2 | 1/2008 | Sharps et al. | 606/32 |
| 7,331,956 B2 | 2/2008 | Hovda et al. | 606/32 |
| RE40,156 E | 3/2008 | Sharps et al. | 606/32 |
| 7,357,798 B2 | 4/2008 | Sharps et al. | 606/32 |
| 7,387,625 B2 | 6/2008 | Hovda et al. | 606/32 |
| 7,419,488 B2 | 9/2008 | Ciarrocca et al. | 606/41 |
| 7,429,260 B2 | 9/2008 | Underwood et al. | 606/32 |
| 7,429,262 B2 | 9/2008 | Woloszko et al. | 606/46 |
| 7,435,247 B2 | 10/2008 | Woloszko et al. | 604/45 |
| 7,442,191 B2 | 10/2008 | Hovda et al. | 606/41 |
| 7,445,618 B2 | 11/2008 | Eggers et al. | 604/48 |
| 7,449,021 B2 | 11/2008 | Underwood et al. | 606/32 |
| 7,462,178 B2 | 12/2008 | Woloszko et al. | 607/105 |
| 7,468,059 B2 | 12/2008 | Eggers et al. | 606/32 |
| 7,491,200 B2 | 2/2009 | Underwood et al. | 606/32 |
| 7,507,236 B2 | 3/2009 | Eggers et al. | 606/41 |
| 7,572,251 B1 | 8/2009 | Davison et al. | 604/500 |
| 7,632,267 B2 | 12/2009 | Dahla | 606/41 |
| 7,691,101 B2 | 4/2010 | Davison et al. | 606/41 |
| 7,704,249 B2 | 4/2010 | Woloszko et al. | 606/48 |
| 7,708,733 B2 | 5/2010 | Sanders et al. | 606/41 |
| 8,083,736 B2* | 12/2011 | McClurken | A61B 17/32 606/41 |
| 2002/0029036 A1 | 3/2002 | Goble et al. | 606/38 |
| 2002/0049438 A1 | 4/2002 | Sharkey et al. | 606/41 |
| 2002/0058933 A1* | 5/2002 | Christopherson et al. | 606/34 |
| 2002/0193787 A1* | 12/2002 | Qin et al. | 606/34 |
| 2003/0013986 A1 | 1/2003 | Saadat | 600/549 |
| 2003/0028189 A1* | 2/2003 | Woloszko | A61B 18/14 606/45 |
| 2003/0088245 A1 | 5/2003 | Woloszko et al. | 606/41 |
| 2003/0130655 A1 | 7/2003 | Woloszko et al. | 606/45 |
| 2003/0158545 A1 | 8/2003 | Hovda et al. | 606/32 |
| 2003/0171743 A1 | 9/2003 | Tasto et al. | 606/32 |
| 2003/0208196 A1 | 11/2003 | Stone | 606/41 |
| 2003/0212396 A1 | 11/2003 | Eggers et al. | 606/41 |
| 2004/0044339 A1* | 3/2004 | Beller et al. | 606/34 |
| 2004/0054365 A1* | 3/2004 | Goble | 606/34 |
| 2004/0116922 A1 | 6/2004 | Hovda et al. | 606/41 |
| 2004/0127893 A1 | 7/2004 | Hovda | 606/41 |
| 2004/0230190 A1 | 11/2004 | Dahla et al. | 604/41 |
| 2005/0004634 A1 | 1/2005 | Hovda et al. | 606/41 |
| 2005/0261754 A1 | 11/2005 | Woloszko et al. | 606/32 |
| 2005/0288665 A1 | 12/2005 | Woloszko et al. | 606/41 |
| 2006/0036237 A1 | 2/2006 | Davison et al. | 606/41 |
| 2006/0095031 A1 | 5/2006 | Ormsby | 606/34 |
| 2006/0178670 A1 | 8/2006 | Woloszko et al. | 606/48 |
| 2006/0189971 A1 | 8/2006 | Eggers et al. | 606/32 |
| 2006/0217707 A1* | 9/2006 | Daniel | A61B 18/1477 606/50 |
| 2006/0253117 A1 | 11/2006 | Hovda et al. | 128/898 |
| 2006/0259025 A1 | 11/2006 | Dahla | 607/108 |
| 2007/0106288 A1 | 5/2007 | Woloszko et al. | 606/41 |
| 2007/0149966 A1 | 6/2007 | Dahla et al. | 606/41 |
| 2007/0161981 A1 | 7/2007 | Sanders et al. | 606/41 |
| 2007/0208334 A1 | 9/2007 | Woloszko et al. | 606/41 |
| 2007/0208335 A1 | 9/2007 | Woloszko et al. | 606/41 |
| 2007/0282323 A1 | 12/2007 | Woloszko et al. | 606/41 |
| 2008/0167645 A1* | 7/2008 | Woloszko | A61B 18/1206 606/40 |
| 2014/0324039 A1* | 10/2014 | Malackowski et al. | 606/34 |

FOREIGN PATENT DOCUMENTS

| | | | |
|---|---|---|---|
| EP | 0740926 A2 | 11/1996 | A61B 17/39 |
| EP | 0754437 A2 | 1/1997 | A61B 17/39 |
| EP | 0694290 B1 | 11/2000 | A61B 18/04 |
| FR | 2313949 | 1/1977 | A61N 3/02 |
| GB | 2 308 979 | 7/1997 | A61B 17/36 |
| GB | 2 308 980 | 7/1997 | A61B 17/36 |
| GB | 2 308 981 | 7/1997 | A61B 17/36 |
| GB | 2 327 350 | 1/1999 | A61B 17/39 |
| GB | 2 327 351 | 1/1999 | A61B 17/39 |
| GB | 2 327 352 | 1/1999 | A61B 17/39 |
| JP | 57-57802 | 4/1982 | A61B 1/00 |
| JP | 57-117843 | 7/1982 | A61B 17/39 |
| JP | 58-13213 | 1/1983 | A61B 18/12 |
| JP | 10-43198 | 2/1998 | A61B 17/42 |
| WO | 90/03152 | 4/1990 | A61B 17/39 |
| WO | 90/07303 | 7/1990 | A61B 17/39 |
| WO | 92/21278 | 12/1992 | A61B 5/04 |
| WO | 93/13816 | 7/1993 | A61B 17/36 |
| WO | 93/20747 | 10/1993 | A61B 5/00 |
| WO | 94/04220 | 3/1994 | |
| WO | 94/08654 | 4/1994 | A61M 37/00 |
| WO | 94/10924 | 5/1994 | A61B 17/39 |
| WO | 94/26228 | 11/1994 | A61G 17/36 |
| WO | 95/34259 | 12/1995 | A61F 5/48 |
| WO | 96/00042 | 1/1996 | A61B 17/39 |
| WO | 96/37156 | 11/1996 | A61B 17/00 |
| WO | 96/39914 | 12/1996 | A61B 1/00 |
| WO | 97/00646 | 1/1997 | A61B 17/39 |
| WO | 97/00647 | 1/1997 | A61B 17/39 |
| WO | 97/15237 | 5/1997 | A61B 18/12 |
| WO | 97/18765 | 5/1997 | A61B 17/36 |
| WO | 97/24073 | 7/1997 | A61B 17/39 |
| WO | 97/24074 | 7/1997 | A61B 17/39 |
| WO | 97/24993 | 7/1997 | A61B 17/39 |
| WO | 97/24994 | 7/1997 | A61B 17/39 |
| WO | 97/30644 | 8/1997 | A61B 17/39 |
| WO | 97/30645 | 8/1997 | A61B 17/39 |
| WO | 97/30646 | 8/1997 | A61B 17/39 |
| WO | 97/30647 | 8/1997 | A61B 17/39 |
| WO | 97/41785 | 11/1997 | A61B 17/39 |
| WO | 97/41786 | 11/1997 | A61B 17/39 |
| WO | 97/41787 | 11/1997 | A61B 17/39 |
| WO | 97/41788 | 11/1997 | A61B 17/39 |
| WO | 97/43969 | 11/1997 | A61B 17/39 |
| WO | 97/43970 | 11/1997 | A61B 17/39 |
| WO | 97/43972 | 11/1997 | A61B 17/39 |
| WO | 97/43973 | 11/1997 | A61B 17/39 |

(56) References Cited

FOREIGN PATENT DOCUMENTS

| WO | 97/44092 | 11/1997 | ............ A61B 17/39 |
| WO | 97/48345 | 12/1997 | ............ A61B 17/39 |
| WO | 97/48346 | 12/1997 | ............ A61B 17/39 |
| WO | 98/07468 | 2/1998 | ............ A61N 1/40 |
| WO | 98/27879 | 7/1998 | ............ A61B 17/36 |
| WO | 98/27880 | 7/1998 | ............ A61B 17/39 |
| WO | 99/08613 | 2/1999 | ............ A61B 17/36 |
| WO | 99/09919 | 3/1999 | ............ A61B 18/12 |
| WO | 99/17690 | 4/1999 | ............ A61F 7/12 |
| WO | 99/30655 | 6/1999 | ............ A61F 7/12 |
| WO | 99/51155 | 10/1999 | ............ A61B 17/36 |
| WO | 99/51158 | 10/1999 | ............ A61B 17/39 |
| WO | 00/62698 | 10/2000 | ............ A61B 18/14 |
| WO | 01/87154 | 5/2001 | ............ A61B 5/05 |
| WO | 02/36028 | 5/2002 | ............ A61B 18/12 |
| WO | 04/50171 | 6/2004 | |
| WO | 05/125287 | 12/2005 | ............ A61B 18/00 |
| WO | 06/002337 | 1/2006 | ............ A61B 18/14 |
| WO | 06/125007 | 11/2006 | ............ A61B 18/14 |

OTHER PUBLICATIONS

BiLAP Generator Settings, Jun. 1991.

BiLAP IFU 910026-001 Rev A for BiLAP Model 3525, J-Hook, 4 pgs, May 20, 1991.

BiLAP IFU 910033-002 Rev A for BiLAP Model 3527, L-Hook; BiLAP Model 3525, J-Hook; BiLAP Model 3529, High Angle, 2 pgs, Nov. 30, 1993.

Codman & Shurtleff, Inc. "The Malis Bipolar Coagulating and Bipolar Cutting System CMC—II" brochure, early, 2 pgs, 1991.

Codman & Shurtleff, Inc. "The Malis Bipolar Electrosurgical System CMC—III Instruction Manual" , 15 pgs, Jul. 1991.

Cook et al., "Therapeutic Medical Devices: Application and Design", Prentice Hall, Inc., 3pgs, 1982.

Dennis et al. "Evolution of Electrofulguration in Control of Bleeding of Experimental Gastric Ulcers," Digestive Diseases and Sciences, vol. 24, No. 11, 845-848, Nov. 1979.

Dobbie, A.K., "The Electrical Aspects of Surgical Diathermy, Bio Medical Engineering" Bio-Medical Engineering vol. 4, pp. 206-216, May 1969.

Elsasser, V.E. et al., "An Instrument for Transurethral Resection without Leakage of Current" Acta Medicotechnica vol. 24, No. 4, pp. 129-134, 1976.

Geddes, "Medical Device Accidents: With Illustrative Cases" CRC Press, 3 pgs, 1998.

Honig, W., "The Mechanism of Cutting in Electrosurgery" IEEE pp. 58-65, 1975.

Kramolowsky et al. "The Urological App of Electorsurgery" J. of Urology vol. 146, pp. 669-674, 1991.

Kramolowsky et al. "Use of 5F Bipolar Electrosurgical Probe in Endoscopic Urological Procedures" J. of Urology vol. 143, pp. 275-277, 1990.

Lee, B et al. "Thermal Compression and Molding of Artherosclerotic Vascular Tissue with Use" JACC vol. 13(5), pp. 1167-1171, 1989.

Letter from Department of Health to Jerry Malis dated Jan. 24, 1991, 3 pgs.

Letter from Department of Health to Jerry Malis dated Jul. 25, 1985, 1 pg.

Letter from Jerry Malis to FDA dated Jul. 25, 1985, 2 pgs.

Lu, et al., "Electrical Thermal Angioplasty: Catheter Design Features, In Vitro Tissue Ablation Studies and In Vitro Experimental Findings," Am J. Cardiol vol. 60, pp. 1117-1122, Nov. 1, 1987.

Malis, L., "Electrosurgery, Technical Note," J. Neursurg., vol. 85, pp. 970-975, Nov. 1996.

Malis, L., "Excerpted from a seminar by Leonard I. Malis, M.D. at the 1995 American Association of Neurological Surgeons Meeting," 1pg, 1995.

Malis, L., "Instrumentation for Microvascular Neurosurgery" Cerebrovascular Surgery, vol. 1, pp. 245-260, 1985.

Malis, L., "New Trends in Microsurgery and Applied Technology," Advanced Technology in Neurosurgery, pp. 1-16, 1988.

Malis, L., "The Value of Irrigation During Bipolar Coagulation" See ARTC 21602, 1 pg, Apr. 9, 1993.

Nardella, P.C., SPIE 1068: pp. 42-49, Radio Frequency Energy and Impedance Feedback, 1989.

O'Malley, Schaum's Outline of Theory and Problems of Basic Circuit Analysis, McGraw-Hill, $2^{nd}$ Ed., pp. 3-5, 1992.

Olsen MD, Bipolar Laparoscopic Cholecstectomy Lecture (marked confidential), 12 pgs, Oct. 7, 1991.

Pearce, John A. "Electrosurgery", pp. 17, 69-75, 87, John Wiley & Sons, New York, 1986.

Pearce, John A., "Electrosurgery", Handbook of Biomedical Engineering, chapter 3, Academic Press Inc., N.Y., pp. 98-113, 1988.

Piercey et al., "Electrosurgical Treatment of Experimental Bleeding Canine Gastric Ulcers" Gastroenterology vol. 74(3), pp. 527-534, 1978.

Protell et al., "Computer-Assisted Electrocoagulation: Bipolar v. Monopolar in the Treatment of Experimental Canine Gastric Ulcer Bleeding," Gastroenterology vol. 80, No. 3, pp. 451-455, 1981.

Ramsey et al., "A Comparison of Bipolar and Monopolar Diathermy Probes in Experimental Animals", Urological Research vol. 13, pp. 99-102, 1985.

Selikowitz et al., "Electric Current and Voltage Recordings on the Myocardium During Electrosurgical Procedures in Canines," Surgery, Gynecology & Obstetrics, vol. 164, pp. 219-224, Mar. 1987.

Shuman, "Bipolar Versus Monopolar Electrosurgery: Clinical Applications," Dentistry Today, vol. 20, No. 12, 7 pgs, Dec. 2001.

Slager et al. "Spark Erosion of Arteriosclerotic Plaques" Z. Kardiol. 76:Suppl. 6, pp. 67-71, 1987.

Slager et al. "Vaporization of Atherosclerotice Plaques by Spark Erosion" JACC 5(6): pp. 1382-1386, Jun. 1985.

Stoffels, E. et al., "Investigation on the Interaction Plasma-Bone Tissue", E-MRS Spring Meeting, 1 pg, Jun. 18-21, 2002.

Stoffels, E. et al., "Biomedical Applications of Plasmas", Tutorial presented prior to the $55^{th}$ Gaseous Electronics Conference in Minneapolis, MN, 41 pgs, Oct. 14, 2002.

Stoffels, E. et al., "Plasma Interactions with Living Cells", Eindhoven University of Technology, 1 pg, 2002.

Stoffels, E. et al., "Superficial Treatment of Mammalian Cells using Plasma Needle", J. Phys. D: Appl. Phys. 26, pp. 2908-2913, Nov. 19, 2003.

Stoffels, E. et al., "Plasma Needle", Eindhoven University of Technology, 1 pg, Nov. 28, 2003.

Stoffels, E. et al., "Plasma Physicists Move into Medicine", Physicsweb, 1 pg, Nov. 2003.

Stoffels, E. et al., "Plasma Treated Tissue Engineered Skin to Study Skin Damage", Biomechanics and Tissue Engineering, Materials Technology, 1 pg, 2003.

Stoffels, E. et al., "Plasma Treatment of Dental Cavities: A Feasibility Study", IEEE Transaction on Plasma Science, vol. 32, No. 4, pp. 1540-1542, Aug. 2004.

Stoffels, E. et al., "The Effects of UV Irradiation and Gas Plasma Treatment on Living Mammalian Cells and Bacteria: A Comparative Approach", IEEE Transaction on Plasma Science, vol. 32, No. 4, pp. 1544-1550, Aug. 2004.

Stoffels, E. et al., "Electrical and Optical Characterization of the Plasma Needle", New Journal of Physics 6, pp. 1-14, Oct. 28, 2004.

Stoffels, E. et al., "Where Plasma Meets Plasma", Eindhoven University of Technology, 23 pgs, 2004.

Stoffels, E. et al., "Gas Plasma effects on Living Cells", Physica Scripta, T107, pp. 79-82, 2004.

Stoffels, E. et al., "Plasma Treatment of Mammalian Vascular Cells: A Quantitative Description", IEEE Transaction on Plasma Science, vol. 33, No. 2, pp. 771-775, Apr. 2005.

Stoffels, E. et al., "Deactivation of Escherichia coli by the Plasma Needle", J. Phys. D: Appl. Phys. 38, pp. 1716-1721, May 20, 2005.

Stoffels, E. et al., "Development of a Gas Plasma Catheter for Gas Plasma Surgery", XXVIIth ICPIG, Endoven University of Technology, pp. 18-22, Jul. 2005.

Stoffels, E. et al., "Development of a Smart Positioning Sensor for the Plasma Needle", Plasma Sources Sci. Technol. 15, pp. 582-589, Jun. 27, 2006.

(56) References Cited

OTHER PUBLICATIONS

Stoffels, E. et al., Killing of *S. mutans* Bacteria Using a Plasma Needle at Atmospheric Pressure, IEEE Transaction on Plasma Science, vol. 34, No. 4, pp. 1317-1324, Aug. 2006.
Stoffels, E. et al., "Plasma-Needle Treatment of Substrates with Respect to Wettability and Growth of *Excherichia coli* and *Streptococcus mutans*", IEEE Transaction on Plasma Science, vol. 34, No. 4, pp. 1325-1330, Aug. 2006.
Stoffels, E. et al., "Reattachment and Apoptosis after Plasma-Needle Treatment of Cultured Cells", IEEE Transaction on Plasma Science, vol. 34, No. 4, pp. 1331-1336, Aug. 2006.
Stoffels, E. et al., "UV Excimer Lamp Irradiation of Fibroblasts: The Influence on Antioxidant Homostasis", IEEE Transaction on Plasma Science, vol. 34, No. 4, pp. 1359-1364, Aug. 2006.
Stoffels, E. et al., "Plasma Needle for In Vivo Medical Treatment: Recent Developments and Perspectives", Plasma Sources Sci. Technol. 15, pp. S169-S180, Oct. 6, 2006.
Swain, C.P., et al., "Which Electrode, A Comparison of four endoscopic methods of electrocoagulation in experimental bleeding ulcers" *Gut* vol. 25, pp. 1424-1431, 1987.
Tucker, R. et al., Abstract P14-11, p. 248, "A Bipolar Electrosurgical Turp Loop", Nov. 1989.
Tucker, R. et al. "A Comparison of Urologic Application of Bipolar Versus Monopolar Five French Electrosurgical Probes" *J. of Urology* vol. 141, pp. 662-665, 1989.
Tucker, R. et al. "In vivo effect of 5 French Bipolar and Monopolar Electrosurgical Probes on the Porcine Bladder" *Urological Research* vol. 18, pp. 291-294, 1990.
Tucker, R. et al., "Demodulated Low Frequency Currents from Electrosurgical Procedures," *Surgery, Gynecology and Obstetrics*, 159:39-43, 1984.
Tucker et al. "The interaction between electrosurgical generators, endoscopic electrodes, and tissue," Gastrointestinal Endoscopy, vol. 38, No. 2, pp. 118-122, 1992.
Valley Forge Scientific Corp., "Summary of Safety and Effective Information from 510K", 2pgs, 1991.
Valley Forge's New Products, Clinica, 475, 5, Nov. 6, 1991.
Valleylab SSE2L Instruction Manual, 11 pgs, Jan. 6, 1983.
Valleylab, Inc. "Valleylab Part No. 945 100 102 A" Surgistat Service Manual, pp. 1-46, Jul. 1988.
Wattiez, Arnaud et al., "Electrosurgery in Operative Endoscopy," Electrosurgical Effects, Blackwell Science, pp. 85-93, 1995.
Wyeth, "Electrosurgical Unit" pp. 1181-1202, 2000.
Rand et al., "Effect of Elecctrocautery on Fresh Human Articular Cartilage", J. Arthro. Surg., vol. 1, pp. 242-246, 1985.
European Search Report for EP00123324.6 4 pgs, dated Jan. 16, 2001.
European Search Report for EP00928246 4 pgs, dated Mar. 7, 2008.
European Search Report for EP09153983 9 pgs, dated Apr. 1, 2009.
European Search Report for EP98964730.0 3 pgs, dated Nov. 20, 2000.
European Search Report for EP99922855.4 3 pgs, dated Aug. 2, 2001.
European Search Reprot for EP05762588 3 pgs, dated Apr. 12, 2010.
PCT International Preliminary Examination Report for PCT/US00/10674 4pgs, dated Mar. 7, 2001.
PCT International Preliminary Examination Report for PCT/US98/26624 4pgs, dated Oct. 12, 1999.
PCT International Preliminary Examination Report for PCT/US99/10062 3pgs, dated Jun. 20, 2000.
PCT International Preliminary Report on Patentability for PCT/US05/22373 4pgs, dated Dec. 28, 2006.
PCT International Preliminary Report on Patentability for PCT/US06/19095 6pgs, dated Nov. 20, 2007.
PCT International Search Report for PCT/US00/10674 1 pg, dated Jul. 27, 2000.
PCT International Search Report for PCT/US03/38782 1pg, dated Jun. 30, 2004.
PCT International Search Report for PCT/US05/22373 1 pg, dated Oct. 3, 2006.
PCT International Search Report for PCT/US06/19095 2 pgs, dated Oct. 4, 2007.
PCT International Search Report for PCT/US96/08077 1 page, dated Sep. 16, 1996.
PCT International Search Report for PCT/US98/26624 1 page, dated Mar. 3, 1999.
PCT International Search Report for PCT/US99/10062 1 pg, dated Aug. 23, 1999.
GB Examination Report for GB1111622.5 dated Jul. 29, 2016, 5 pages.

* cited by examiner

ELECTROSURGICAL SYSTEM WITH DEVICE SPECIFIC OPERATIONAL PARAMETERS

FIELD OF THE INVENTION

The present invention relates to an electrosurgical generator used in combination with various types of electrosurgical devices which are connectable to the generator to perform electrosurgical procedures within a patient. More particularly, the present invention relates to an electrosurgical generator that determines one or more operational parameters to perform the electrosurgical procedure based on the specific type of electrosurgical device connected to the generator.

BACKGROUND OF THE INVENTION

The field of electrosurgery includes a number of loosely related surgical techniques which have in common the application of electrical energy to modify the structure or integrity of patient tissue. Electrosurgical procedures usually operate through the application of very high frequency currents to cut or ablate tissue structures, where the operation can be monopolar or bipolar. Monopolar techniques rely on a separate electrode for the return of RF current that is placed away from the surgical site on the body of the patient, and where the surgical device defines only a single electrode pole that provides the surgical effect. Bipolar devices comprise both electrodes for the application of current between their surfaces.

Electrosurgical procedures and techniques are particularly advantageous since they generally reduce patient bleeding and trauma associated with cutting operations. Additionally, electrosurgical ablation procedures, where tissue surfaces and volume may be reshaped, cannot be duplicated through other treatment modalities.

Present electrosurgical techniques used for tissue ablation suffer from an inability to control the depth of necrosis in the tissue being treated. Most electrosurgical devices rely on creation of an electric arc between the treating electrode and the tissue being cut or ablated to cause the desired localized heating. Such arcs, however, often create very high temperatures causing a depth of necrosis greater than 500 µm, frequently greater than 800 µm, and sometimes as great as 1700 µm. The inability to control such depth of necrosis is a significant disadvantage in using electrosurgical techniques for tissue ablation, particularly in arthroscopic, otolaryngological, and spinal procedures.

Radiofrequency (RF) energy is used in a wide range of surgical procedures because it provides efficient tissue resection and coagulation and relatively easy access to the target tissues through a portal or cannula. However, a typical phenomenon associated with the use of RF during these procedures is that the currents used to induce the surgical effect can result in heating of electrically conductive fluid used during the procedure to provide for the ablation and/or to irrigate the treatment site. If the temperature of this fluid were allowed to increase above a threshold temperature value, the heated fluid could result in undesired necrosis or damage to surrounding neuromuscular and/or soft tissue structures.

One attempt to mitigate these damaging effects includes use of a suction lumen on the distal tip of the electrosurgical device to continuously remove the affected fluid from the surgical site and thereby reduce the overall temperature. Typical suction systems utilize a surgical vacuum source that is self-regulated to maintain a pre-set vacuum pressure. Consequently, the pre-set pressure is applied to each and every device regardless of what type of device is being connected. One problem associated with such systems is that the pre-set pressure arising from the vacuum source is not optimized for the specific device and may negatively affect the efficacy of such electrosurgical devices.

U.S. Patent Application Publication No. 2008/0167645 to Woloszko describes a controller that regulates the suction at the site. The controller receives real-time data from the target site and adjusts the flowrate of the suction line based on the data. Though the controller described in the Woloszko Publication addresses suction, it does not determine and control a number of other device specific operational parameters which may affect clinical efficacy.

Another attempt to mitigate the above described damaging effects includes limiting power output. Typically, an electrosurgical generator includes a user interface which allows the user to adjust various power settings, namely, voltage, current, and power. Limiting power output, however, is not always desirable. One power level may be suitable for one type of device and unsuitable for another type of device. Consequently, a pre-set power level without reference to the type of ablation device is not optimal.

An improved generator (The Quantum™ Generator manufactured by ArthroCare Corporation, Austin Tex.) addresses the above described shortcoming. The Quantum Generator is operable to identify the type of ablation device and determine default voltage settings. This provides a fine approach for a number of procedures such as arthroscopic procedures.

However, it is still desirable to determine and control additional operational parameters. Failure to account or control certain operational parameters (e.g., the flowrate of electrically conductive fluid delivered to the target site) can reduce the efficiency of ablation and treatment or lead to undesirable heating of the tissue. In certain open and semi-open procedures such as ENT and spine procedures, a conductive fluid is required to be delivered to the operating field. The conductive fluid is typically provided via a gravity feed or by a separate fluid delivery pump: in either instance the flow rate of the conductive fluid is set manually and often varies from user to user and procedure to procedure. This variability can lead to less than optimal ablation and heating of the tissue.

Accordingly, improved systems and methods are still desired for the electrosurgical ablation and cutting of tissue and in particular, improved systems operable to automatically identify various device specific operational parameters such as flowrate when the ablation device is connected to the generator.

SUMMARY OF THE INVENTION

An electrosurgical system for treating tissue at a target site includes at least one type of electrosurgical device and a generator adapted to connect with the device. The generator comprises a high frequency power supply for delivery of high frequency energy to the active electrode terminal and a return electrode and a fluid control device for driving electrically conductive fluid to the target site. The controller is operable to identify the device type when the device is operationally connected to the generator and to automatically determine an operational parameter specific to the device type. The operational parameter comprises a candidate flowrate for delivering the electrically conductive fluid.

In one embodiment the controller identifies the device type based on an electrical resistance associated with the device when the device is connected to the generator.

The device specific operational parameters of the present invention may vary widely. In one embodiment the device specific operational parameter is flowrate. The controller is adapted to determine at least 3 different candidate flowrates for delivering electrically conductive fluid to the target site based on the device type. A maximum, minimum and initial flowrate may be determined. In another embodiment, the minimum candidate flowrate is 45 milliliters per minute, and the maximum candidate flowrate is 65 milliliters per minute.

In another embodiment, the controller comprises a library of preselected candidate operational parameters and in one preferred embodiment, a library of preselected candidate flowrates corresponding to a plurality of types of devices.

In another embodiment, the operational parameter comprises one or more of the following: alarm condition, energy stop condition, count or beep duration, and device activation duration. The alarm condition causes an alarm signal when the alarm condition is met. The energy stop condition causes energy output to be halted or suspended based on at least one of the following: a) output current of the device, and b) total time that the device is connected to the generator.

In another embodiment, the operational parameter comprises a periodic counter (or beeper) duration based on the device type and the controller beeps upon the completion of each periodic count duration. This provides the user a sense of elapsed time.

In another embodiment the operational parameter comprises a device activation duration based on the device type and the controller stops delivery of high frequency energy to the device upon completion of the procedure duration. In one embodiment the device activation duration is equal to or greater than 20 seconds and less than or equal to 40 seconds. This is useful in certain procedures.

In another embodiment the controller is operable to pulse the delivery of high frequency energy based on the device type. In another embodiment, the fluid control device is a peristaltic pump.

In another embodiment the system includes a first type of electrosurgical device having an integrated fluid delivery channel or line to provide electrically conductive liquid to the target site.

In another embodiment system includes an electrically conductive fluid supply reservoir that is in fluid communication with the fluid delivery channel. The pump of the system is operable to drive fluid to the site through the channel. The pump is controlled by the generator and set at a flowrate based on the specific type of device being used in the procedure. In another embodiment the candidate flowrate is also based on the energy supplied to the device.

In another embodiment an electrosurgical method to ablate soft tissue at a target site with at least one type of electrosurgical device comprises the following steps: connecting a first type of electrosurgical device with an electrosurgical generator, automatically determining at least one operational parameter based on identifying the electrosurgical device as a first type of electrosurgical device; activating the fluid control device to transport the electrically conductive fluid to the target site at a flowrate; and delivering high frequency energy to an active electrode terminal located at the distal end of the electrosurgical device.

The step of automatically determining may include determining an operational parameter selected from the group consisting of flowrate, alarm conditions, stop conditions, count duration, and device activation duration.

In another embodiment, the step of automatically determining comprises determining at least three candidate flowrates based on the device type. The activating step may be performed by an operator selecting one of the candidate flowrates. In another embodiment the flowrate is also based on an amount of energy delivered to the device.

In another embodiment, the method further comprises detaching the first type of electrosurgical device from the generator and connecting a second type of electrosurgical device to the generator and automatically determining at least one operational parameter based on identifying the electrosurgical device as the second type of electrosurgical device.

In another embodiment the first device is adapted for otolaryngological procedures and the second type of device is configured for ablating soft tissue in the spine.

In another embodiment the method further includes pulsing the high frequency energy based on identifying the device type.

In another embodiment the method further includes pumping the fluid to the target site with a peristaltic pump.

The description, objects and advantages of the present invention will become apparent from the detailed description to follow, together with the accompanying drawings.

DETAILED DESCRIPTION OF THE INVENTION

Figure 1A:
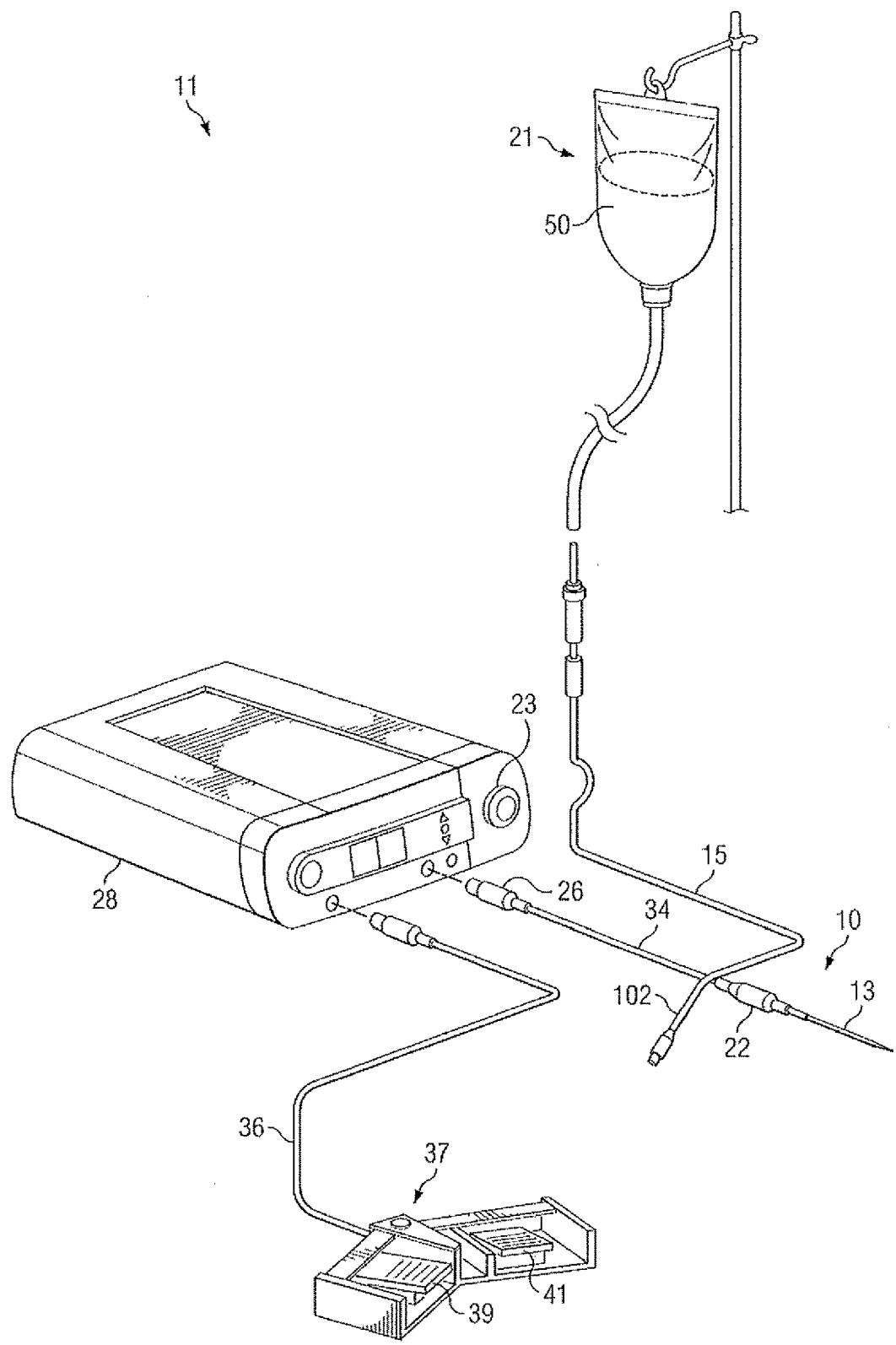
FIG. 1A is a perspective view of an electrosurgical system including an electrosurgical device and electrosurgical generator.

Before the present invention is described in detail, it is to be understood that this invention is not limited to particular variations set forth herein as various changes or modifications may be made to the invention described and equivalents may be substituted without departing from the spirit and scope of the invention. As will be apparent to those of skill in the art upon reading this disclosure, each of the individual embodiments described and illustrated herein has discrete components and features which may be readily separated from or combined with the features of any of the other several embodiments without departing from the scope or spirit of the present invention. In addition, many modifications may be made to adapt a particular situation, material, composition of matter, process, process act(s) or step(s) to the objective(s), spirit or scope of the present invention. All such modifications are intended to be within the scope of the claims made herein.

Methods recited herein may be carried out in any order of the recited events which is logically possible, as well as the recited order of events. Furthermore, where a range of values is provided, it is understood that every intervening value, between the upper and lower limit of that range and any other stated or intervening value in that stated range is encompassed within the invention. Also, it is contemplated that any optional feature of the inventive variations described may be set forth and claimed independently, or in combination with any one or more of the features described herein.

All existing subject matter mentioned herein (e.g., publications, patents, patent applications and hardware) is incorporated by reference herein in its entirety except insofar as the subject matter may conflict with that of the present invention (in which case what is present herein shall prevail). The referenced items are provided solely for their disclosure prior to the filing date of the present application. Nothing herein is to be construed as an admission that the present invention is not entitled to antedate such material by virtue of prior invention.

Reference to a singular item, includes the possibility that there are plural of the same items present. More specifically, as used herein and in the appended claims, the singular forms "a," "an," "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. It is also to be appreciated that unless defined otherwise, all technical and scientific terms used herein have the same meaning as commonly understood by one of ordinary skill in the art to which this invention belongs.

The treatment device of the present invention may have a variety of configurations. However, one variation of the device employs a treatment device using Coblation® technology.

The assignee of the present invention developed Coblation® technology. Coblation® technology involves the application of a high frequency voltage difference between one or more active electrode(s) and one or more return electrode(s) to develop high electric field intensities in the vicinity of the target tissue. The high electric field intensities may be generated by applying a high frequency voltage that is sufficient to vaporize an electrically conductive fluid over at least a portion of the active electrode(s) in the region between the tip of the active electrode(s) and the target tissue. The electrically conductive fluid may be a liquid or gas, such as isotonic saline, blood, extracellular or intracellular fluid, delivered to, or already present at, the target site, or a viscous fluid, such as a gel, applied to the target site.

When the conductive fluid is heated enough such that atoms vaporize off the surface faster than they recondense, a gas is formed. When the gas is sufficiently heated such that the atoms collide with each other causing a release of electrons in the process, an ionized gas or plasma is formed (the so-called "fourth state of matter"). Generally speaking, plasmas may be formed by heating a gas and ionizing the gas by driving an electric current through it, or by shining radio waves into the gas. These methods of plasma formation give energy to free electrons in the plasma directly, and then electron-atom collisions liberate more electrons, and the process cascades until the desired degree of ionization is achieved. A more complete description of plasma can be found in Plasma Physics, by R. J. Goldston and P. H. Rutherford of the Plasma Physics Laboratory of Princeton University (1995), the complete disclosure of which is incorporated herein by reference.

As the density of the plasma or vapor layer becomes sufficiently low (i.e., less than approximately 1020 atoms/$cm^3$ for aqueous solutions), the electron mean free path increases to enable subsequently injected electrons to cause impact ionization within the vapor layer. Once the ionic particles in the plasma layer have sufficient energy, they accelerate towards the target tissue. Energy evolved by the energetic electrons (e.g., 3.5 eV to 5 eV) can subsequently bombard a molecule and break its bonds, dissociating a molecule into free radicals, which then combine into final gaseous or liquid species. Often, the electrons carry the electrical current or absorb the radio waves and, therefore, are hotter than the ions. Thus, the electrons, which are carried away from the tissue towards the return electrode, carry most of the plasma's heat with them, allowing the ions to break apart the tissue molecules in a substantially non-thermal manner.

By means of this molecular dissociation (rather than thermal evaporation or carbonization), the target tissue structure is volumetrically removed through molecular disintegration of larger organic molecules into smaller molecules and/or atoms, such as hydrogen, oxygen, oxides of carbon, hydrocarbons and nitrogen compounds. This molecular disintegration completely removes the tissue structure, as opposed to dehydrating the tissue material by the removal of liquid within the cells of the tissue and extracellular fluids, as is typically the case with electrosurgical desiccation and vaporization. A more detailed description of this phenomena can be found in commonly assigned U.S. Pat. No. 5,697,882, the complete disclosure of which is incorporated herein by reference.

In some applications of the Coblation® technology, high frequency (RF) electrical energy is applied in an electrically conducting media environment to shrink or remove (i.e., resect, cut, or ablate) a tissue structure and to seal transected vessels within the region of the target tissue. Coblation® technology is also useful for sealing larger arterial vessels, e.g., on the order of about 1 mm in diameter. In such applications, a high frequency power supply is provided having an ablation mode, wherein a first voltage is applied to an active electrode sufficient to effect molecular dissociation or disintegration of the tissue, and a coagulation mode, wherein a second, lower voltage is applied to an active electrode (either the same or a different electrode) sufficient to heat, shrink, and/or achieve hemostasis of severed vessels within the tissue.

The amount of energy produced by the Coblation® device may be varied by adjusting a variety of factors, such as: the number of active electrodes; electrode size and spacing; electrode surface area; asperities and sharp edges on the electrode surfaces; electrode materials; applied voltage and power; current limiting means, such as inductors; electrical conductivity of the fluid in contact with the electrodes; density of the fluid; and other factors. Accordingly, these factors can be manipulated to control the energy level of the excited electrons. Since different tissue structures have different molecular bonds, the Coblation® device may be configured to produce energy sufficient to break the molecular bonds of certain tissue but insufficient to break the molecular bonds of other tissue. For example, fatty tissue (e.g., adipose) has double bonds that require an energy level substantially higher than 4 eV to 5 eV (typically on the order of about 8 eV) to break. Accordingly, the Coblation® technology generally does not ablate or remove such fatty tissue; however, it may be used to effectively ablate cells to release the inner fat content in a liquid form. Of course, factors may be changed such that these double bonds can also be broken in a similar fashion as the single bonds (e.g., increasing voltage or changing the electrode configuration to increase the current density at the electrode tips). A more complete description of this phenomenon can be found in commonly assigned U.S. Pat. Nos. 6,355,032; 6,149,120 and 6,296,136, the complete disclosures of which are incorporated herein by reference.

The active electrode(s) of a Coblation® device may be supported within or by an inorganic insulating support positioned near the distal end of the instrument shaft. The return electrode may be located on the instrument shaft, on another instrument or on the external surface of the patient (i.e., a dispersive pad). The proximal end of the instrument(s) will include the appropriate electrical connections for coupling the return electrode(s) and the active electrode(s) to a high frequency power supply, such as an electrosurgical generator.

In one example of a Coblation® device for use with the embodiments disclosed herein, the return electrode of the device is typically spaced proximally from the active electrode(s) a suitable distance to avoid electrical shorting between the active and return electrodes in the presence of electrically conductive fluid. In many cases, the distal edge of the exposed surface of the return electrode is spaced about 0.5 mm to 25 mm from the proximal edge of the exposed surface of the active electrode(s), preferably about 1.0 mm to 5.0 mm. Of course, this distance may vary with different voltage ranges, conductive fluids, and depending on the proximity of tissue structures to active and return electrodes. The return electrode will typically have an exposed length in the range of about 1 mm to 20 mm.

A Coblation® treatment device for use according to the present embodiments may use a single active electrode or an array of active electrodes spaced around the distal surface of a catheter or probe. In the latter embodiment, the electrode array usually includes a plurality of independently current-limited and/or power-controlled active electrodes to apply electrical energy selectively to the target tissue while limiting the unwanted application of electrical energy to the surrounding tissue and environment resulting from power dissipation into surrounding electrically conductive fluids, such as blood, normal saline, and the like. The active electrodes may be independently current-limited by isolating the terminals from each other and connecting each terminal to a separate power source that is isolated from the other active electrodes. Alternatively, the active electrodes may be connected to each other at either the proximal or distal ends of the catheter to form a single wire that couples to a power source.

In one configuration, each individual active electrode in the electrode array is electrically insulated from all other active electrodes in the array within the instrument and is connected to a power source which is isolated from each of the other active electrodes in the array or to circuitry which limits or interrupts current flow to the active electrode when low resistivity material (e.g., blood, electrically conductive saline irrigant or electrically conductive gel) causes a lower impedance path between the return electrode and the individual active electrode. The isolated power sources for each individual active electrode may be separate power supply circuits having internal impedance characteristics which limit power to the associated active electrode when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the active electrodes through independently actuatable switches, or by independent current limiting elements, such as inductors, capacitors, resistors and/or combinations thereof. The current limiting elements may be provided in the instrument, connectors, cable, controller, or along the conductive path from the controller to the distal tip of the instrument. Alternatively, the resistance and/or capacitance may occur on the surface of the active electrode(s) due to oxide layers which form selected active electrodes (e.g., titanium or a resistive coating on the surface of metal, such as platinum).

The Coblation® device is not limited to electrically isolated active electrodes, or even to a plurality of active electrodes. For example, the array of active electrodes may be connected to a single lead that extends through the catheter shaft to a power source of high frequency current.

The voltage difference applied between the return electrode(s) and the active electrode(s) will be at high or radio frequency, typically between about 5 kHz and 20 MHz, usually being between about 30 kHz and 2.5 MHz, preferably being between about 50 kHz and 500 kHz, often less than 350 kHz, and often between about 100 kHz and 200 kHz. In some applications, applicant has found that a frequency of about 100 kHz is useful because the tissue impedance is much greater at this frequency. In other applications, such as procedures in or around the heart or head and neck, higher frequencies may be desirable (e.g., 400-600 kHz) to minimize low frequency current flow into the heart or the nerves of the head and neck.

The RMS (root mean square) voltage applied will usually be in the range from about 5 volts to 1000 volts, preferably being in the range from about 10 volts to 500 volts, often between about 150 volts to 400 volts depending on the active electrode size, the operating frequency and the operation mode of the particular procedure or desired effect on the tissue (i.e., contraction, coagulation, cutting or ablation.)

Typically, the peak-to-peak voltage for ablation or cutting with a square wave form will be in the range of 10 volts to 2000 volts and preferably in the range of 100 volts to 1800 volts and more preferably in the range of about 300 volts to 1500 volts, often in the range of about 300 volts to 800 volts peak to peak (again, depending on the electrode size, number of electrons, the operating frequency and the operation mode). Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak (again, these values are computed using a square wave form). Higher peak-to-peak voltages, e.g., greater than about 800 volts peak-to-peak, may be desirable for ablation of harder material, such as bone, depending on other factors, such as the electrode geometries and the composition of the conductive fluid.

As discussed above, the voltage is usually delivered in a series of voltage pulses or alternating current of time varying voltage amplitude with a sufficiently high frequency (e.g., on the order of 5 kHz to 20 MHz) such that the voltage is effectively applied continuously (as compared with, e.g., lasers claiming small depths of necrosis, which are generally pulsed about 10 Hz to 20 Hz). In addition, the duty cycle (i.e., cumulative time in any one-second interval that energy is applied) is on the order of about 50% for the present invention, as compared with pulsed lasers which typically have a duty cycle of about 0.0001%.

The preferred power source may deliver a high frequency current selectable to generate average power levels ranging from several milliwatts to tens of watts per electrode, depending on the volume of target tissue being treated, and/or the maximum allowed temperature selected for the instrument tip. The power source allows the user to select the voltage level according to the specific requirements of a particular neurosurgery procedure, cardiac surgery, arthroscopic surgery, dermatological procedure, ophthalmic procedures, open surgery or other endoscopic surgery procedure. For cardiac procedures and potentially for neurosurgery, the power source may have an additional filter, for filtering leakage voltages at frequencies below 100 kHz, particularly frequencies around 60 kHz. Alternatively, a power source having a higher operating frequency, e.g., 300 kHz to 600 kHz may be used in certain procedures in which stray low frequency currents may be problematic. A description of one suitable power source can be found in commonly assigned U.S. Pat. Nos. 6,142,992 and 6,235,020, the complete disclosure of both patents are incorporated herein by reference for all purposes.

The power source may be current limited or otherwise controlled so that undesired heating of the target tissue or surrounding (non-target) tissue does not occur. Current limiting inductors may be placed in series with each independent active electrode, where the inductance of the inductor is in the range of 10 µH to 50,000 µH, depending on the electrical properties of the target tissue, the desired tissue heating rate and the operating frequency. Alternatively, capacitor-inductor (LC) circuit structures may be employed, as described previously in U.S. Pat. No. 5,697,909, the complete disclosure of which is incorporated herein by reference. Additionally, current-limiting resistors may be selected. Preferably, these resistors will have a large positive temperature coefficient of resistance so that, as the current level begins to rise for any individual active electrode in contact with a low resistance medium (e.g., saline irrigant or blood), the resistance of the current limiting resistor increases significantly, thereby minimizing the power delivery from said active electrode into the low resistance medium (e.g., saline irrigant or blood). Moreover, other treatment modalities may be used in the inventive method either in place of the Coblation® technology or in addition thereto.

FIG. 1A shows an electrosurgical system including an electrosurgical generator 28 and an electrosurgical device such as an electrosurgical probe 10 which is adapted to apply energy to a target tissue. The electrosurgical probe 10 includes an elongated shaft 13 which may be flexible or rigid, with flexible shafts optionally including support cannulas or other structures (not shown). As discussed further herein, the present invention may include a variety of electrode configurations that may be employed with electrosurgical probe 10 (e.g., a single electrode such as a screen electrode or multiple electrodes).

Probe 10 is shown with an integrated cable 34. The cable 34 includes a connector 26 to operably couple the probe 10 and generator 28. Though the probe 10 shown in FIG. 1A includes an integrated cable, the cable need not be integrated with probe. For example, the probe handle may be designed to receive a cable connector such that the cable may be disconnected at the handle 22 of the probe.

The electrosurgical system shown in FIG. 1A also includes a fluid source 21 holding an electrically conductive liquid 50. The fluid source may be an IV bag filled with physiologic saline solution. The electrically conductive liquid travels along a flowpath from the fluid source 21 to the probe 13 via fluid transport line 15. A fluid drive mechanism 23 is disposed within generator 28 and drives the liquid along the flowpath to the target site. The fluid drive mechanism may be a pump such as peristaltic pump. In one embodiment, and with reference to FIGS. 1B-1C, fluid transport line 15 is installed in the generator 28 behind closable door 16. The fluid transport line 15 is removably positioned or installed along a track or recess of the pump 23. The flowrate of the liquid is controlled by the pump, which is controlled by the generator 28.

The electrosurgical system 11 is also shown comprising a suction lumen 102 in fluid communication with the electrosurgical probe 10. Suction lumen is connected to a suction pump (not shown). Suction pump may encompass any suitable fluid transport apparatus such as, for example, a vacuum pump and canister assembly such as may be provided via a wall outlet in a surgical suite.

A foot pedal 37 is shown connected to power supply 28 via cable 36. The foot pedal 37 includes a first pedal 39 and a second pedal 41 for remotely adjusting the energy level applied to electrodes or for selecting an alternate operating mode. For example, depression of pedal 39 and depression of pedal 41 may correspond to activating wand electrodes in an ablation or coagulation mode.

Figure 1B:
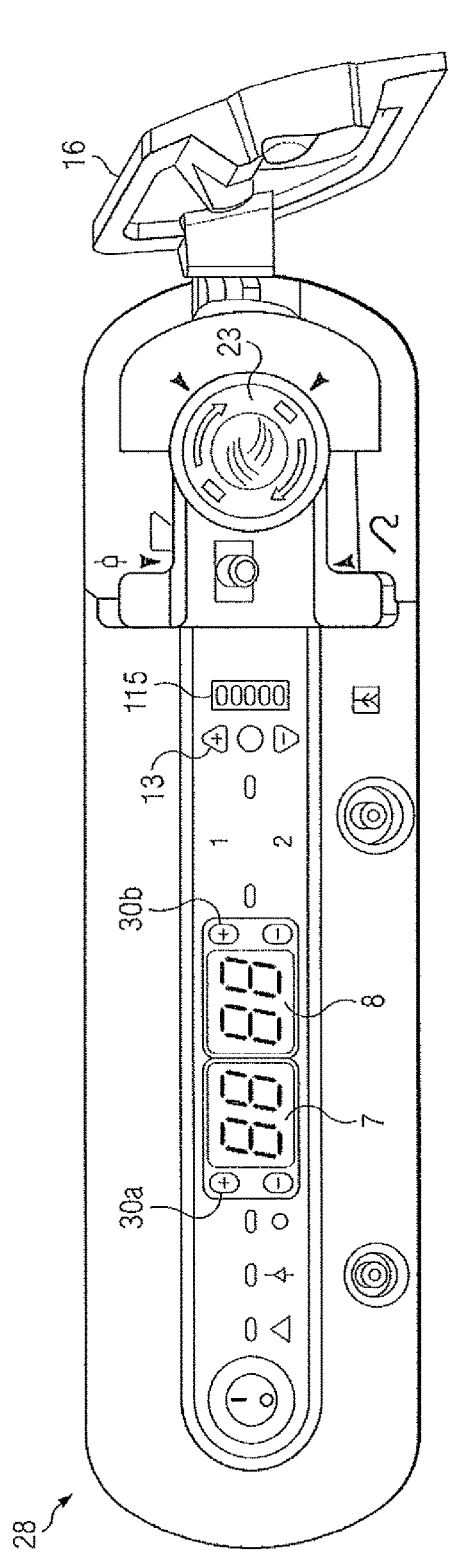
FIG. 1B is a front view of the electrosurgical generator of FIG. 1A including a fluid drive device.
Figure 1C:
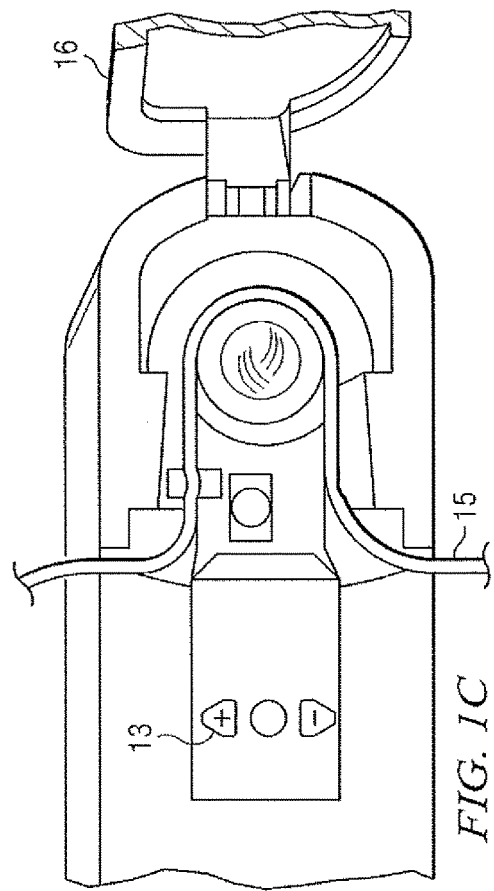
FIG. 1C is a partial view of the electrosurgical generator of FIG. 1B with a fluid transport line installed in the fluid drive device.

With reference to FIG. 1B, generator 28 is shown having one or more buttons or selection means (30a, 30b) to change the applied voltage levels corresponding to ablation modes and coagulation modes respectively. Generator 28 additionally includes a fluid control means 13 for controlling the fluid drive mechanism 23. One or more displays and indicators (7, 8, 115) are provided to indicate energy and fluid transport levels.

As will be discussed further herein, the generator is operable to automatically determine various device specific operational parameters to carry out a procedure. By "device specific operational parameter", it is meant any operational variable, value, setting, or limit specific to the type of electrosurgical device excluding default settings (namely, default voltage levels for RF energy delivery to the electrode elements of the electrosurgical device).

In an application, the generator 28 is connected to the electrosurgical device 13. The generator automatically identifies the type of device and determines at least one device specific operational parameter corresponding to the specific type of device. A mode of operation for the generator related to the operational parameter (e.g., an optimal flowrate specific to the device at which to operate the pump) is automatically and dynamically adjusted not only according to the type of device identified, but may also be adjusted according to an expected procedure type and/or a type of target tissue desired to be treated that is typically associated with the particular selected device. The operating parameter status may then be presented to the operator, and the operator then accepts or modifies the device specific operational parameter and carries out the surgical procedure.

FIGS. 2-6 illustrate various electrosurgical devices or wand configurations. Each wand configuration may be suited for one type of procedure or another. It is to be understood, however, that the type of electrosurgical device that may be used or incorporated into the present invention may vary widely. Presented herein are examples of wands and the invention is not intended to be limited by such embodiments except as specifically limited in the appended claims. Referring to an electrosurgical device 10 in FIGS. 2A and 2B, the electrically isolated electrode terminals 58 are spaced-apart over an electrode array surface 82. The electrode array surface 82 and individual electrode terminals 58 will usually have dimensions within the ranges set forth herein. The electrode array surface 82 has a circular cross-sectional shape with a diameter D (FIG. 2B) in the range from 0.3 mm to 10 mm. Electrode array surface 82 may also have an oval shape. The individual electrode terminals 58 will protrude over the electrode array surface 82 by a distance (H) from 0 mm to 2 mm, preferably from 0 mm to 1 mm (see FIG. 2A).

It should be noted that the electrode terminals may be flush with the electrode array surface 82, or the terminals may be recessed from the surface. For example, in dermatological procedures, the electrode terminals 58 may be recessed by a distance from 0.01 mm to 1 mm, preferably 0.01 mm to 0.2 mm. The electrode terminals may also be axially adjustable relative to the electrode array surface 82 so that the surgeon can adjust the distance between the surface and the electrode terminals.

The electrode terminals 58 are preferably composed of a refractory, electrically conductive metal or alloy, such as platinum, titanium, tantalum, tungsten and the like. As shown in FIG. 2B, the electrode terminals 58 are anchored in a support matrix 48 of suitable insulating material (e.g., ceramic or glass material, such as alumina, zirconia and the like) which could be formed at the time of manufacture in a flat, hemispherical or other shape according to the requirements of a particular procedure. A preferred support matrix material is alumina, available from Kyocera Industrial Ceramics Corporation, Elkgrove, Ill., because of its high thermal conductivity, good electrically insulative properties, high flexural modulus, resistance to carbon tracking, biocompatibility, and high melting point.

Figure 2A:
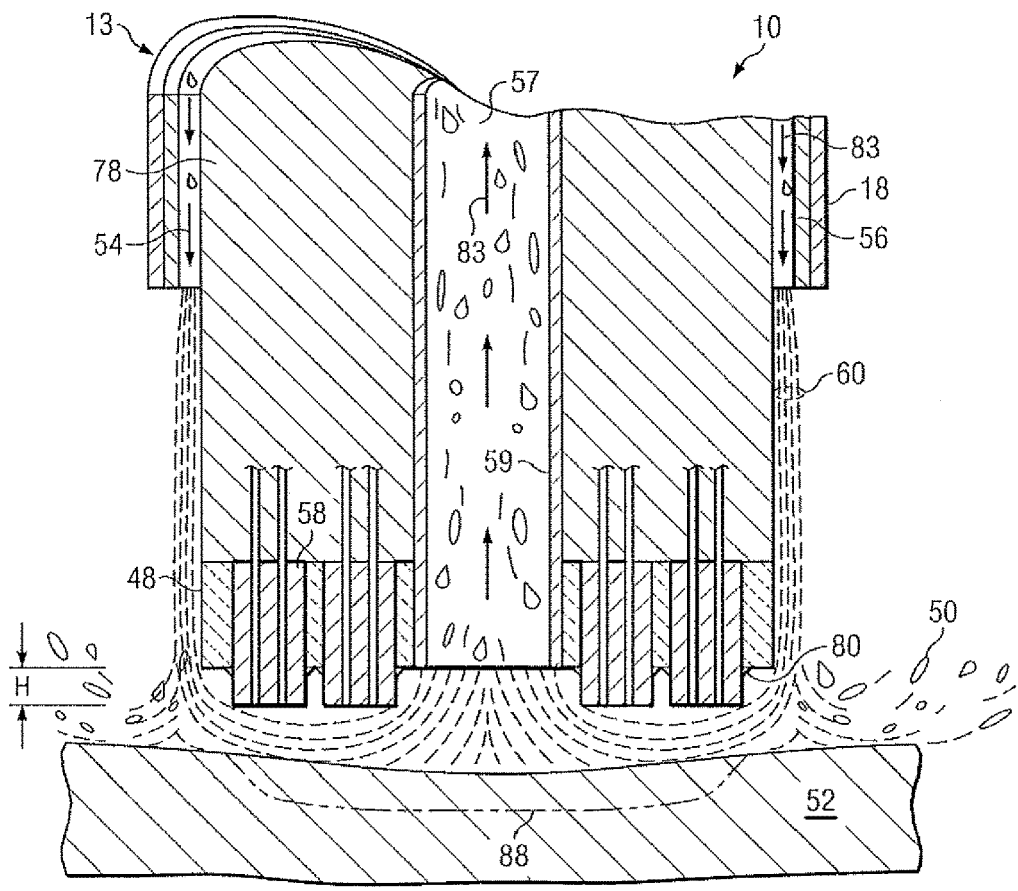
FIG. 2A is side view of an electrosurgical probe.
Figure 2B:
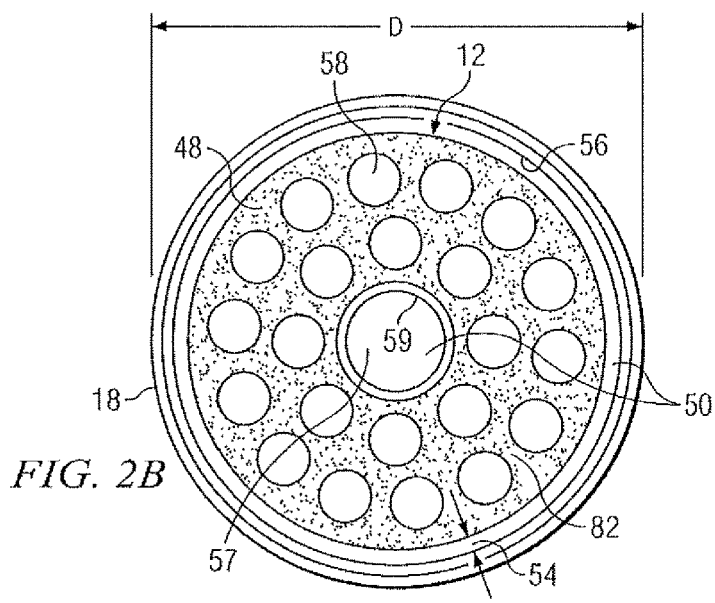
FIG. 2B is an end view of the electrosurgical probe of FIG. 2A.

As shown in FIG. 2A, the support matrix 48 is adhesively joined to a tubular support member 78 that extends most or all of the distance between matrix 48 and the proximal end of probe 10. Tubular member 78 preferably comprises an electrically insulating material, such as an epoxy, injection moldable plastic or silicone-based material. In a preferred construction technique, electrode terminals 58 extend through pre-formed openings in the support matrix 48 so that they protrude above electrode array surface 82 by the desired distance H (FIG. 2A). The electrodes may then be bonded to the distal surface 82 of support matrix 48, typically by an inorganic sealing material 80. Sealing material 80 is selected to provide effective electrical insulation, and good adhesion to both the ceramic matrix 48 and the platinum or titanium electrode terminals. Sealing material 80 additionally should have a compatible thermal expansion coefficient and a melting point well below that of platinum or titanium and alumina or zirconia, typically being a glass or glass ceramic.

In the probe shown in FIGS. 2A and 2B, probe 10 includes a return electrode 56 for completing the current path between electrode terminals 58 and power supply 28. Return electrode 56 is preferably an annular member positioned around the exterior of shaft 13 of probe 10. Return electrode 56 may fully or partially circumscribe tubular support member 78 to form an annular gap 54 therebetween for flow of electrically conducting liquid 50 therethrough. Gap 54 preferably has a width in the range of 0.15 mm to 4 mm. Return electrode 56 extends from the proximal end of probe 10, where it is suitably connected to power supply 28 via connector 26 (shown in FIG. 1), to a point slightly proximal of electrode array surface 82, typically about 0.5 to 10 mm and more preferably about 1 to 10 mm.

Return electrode 56 is disposed within an electrically insulative jacket 18, which is typically formed as one or more electrically insulative sheaths or coatings, such as polytetrafluoroethylene, polyimide, and the like. The provision of the electrically insulative jacket 18 over return electrode 56 prevents direct electrical contact between return electrode 56 and any adjacent body structure or the surgeon. Such direct electrical contact between a body structure (e.g., tendon) and an exposed common electrode member 56 could result in unwanted heating and necrosis of the structure at the point of contact causing necrosis.

Return electrode 56 is preferably formed from an electrically conductive material, usually metal, which is selected from the group consisting of stainless steel alloys, platinum or its alloys, titanium or its alloys, molybdenum or its alloys, and nickel or its alloys. The return electrode 56 may be composed of the same metal or alloy which forms the electrode terminals 58 to minimize any potential for corrosion or the generation of electrochemical potentials due to the presence of dissimilar metals contained within an electrically conductive fluid 50, such as isotonic saline (discussed in greater detail below).

As shown in FIG. 2A, return electrode 56 is not directly connected to electrode terminals 58. To complete this current path so that terminals 58 are electrically connected to return electrode 56 via target tissue 52, electrically conducting liquid 50 (e.g., isotonic saline) is caused to flow along liquid paths 83. A liquid path 83 is formed by annular gap 54 between outer return electrode 56 and tubular support member 78. An additional fluid transport lumen 57 within an inner tubular member 59 is provided to communicate with a fluid transport apparatus or suction source (such as suction pump not shown here) via suction lumen 102 and to remove tissue and other material from the treatment site. In some embodiments, fluid transport lumen 57 may optionally be used to supply conductive fluid to a treatment site.

When a voltage difference is applied between electrode array 12 and return electrode 56, high electric field intensities will be generated at the distal tips of terminals 58 with current flow from array 12 through the target tissue to the return electrode, the high electric field intensities causing ablation of tissue 52 in zone 88. Operating parameters of power supply 28 or probe 10 are preferably monitored by controller (not shown here) during operation thereof and suction is applied via suction pump (not shown here) at a desired flow rate and/or pressure to remove the ablated tissue and other material from the treatment site in order to maintain stable plasma field and associated vapor layer conditions.

Figure 3:
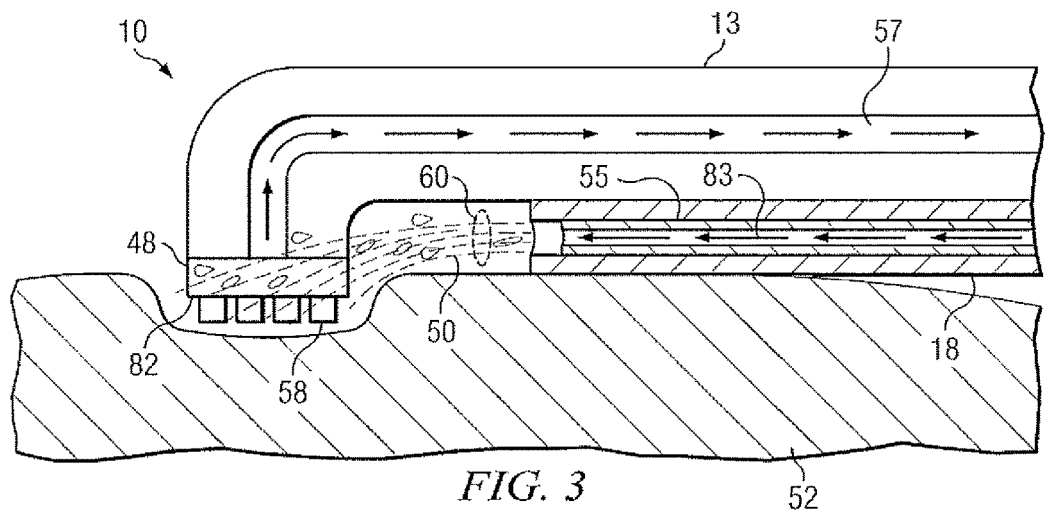
FIG. 3 illustrates an electrosurgical probe where the distal portion of the shaft has an angle.

FIG. 3 illustrates another probe 10 where the distal portion of shaft 13 is bent so that electrode terminals extend transversely to the shaft. Preferably, the distal portion of shaft 13 is perpendicular to the rest of the shaft so that electrode surface 82 is generally parallel to the shaft axis, as shown in FIG. 3. In this embodiment, return electrode 55 is mounted to the outer surface of shaft 13 and is covered with an electrically insulating jacket 18. The electrically conducting fluid 50 flows along flow path 83 through return electrode 55 and exits the distal end of electrode 55 at a point proximal of electrode surface 82. The fluid is directed exterior of shaft to electrode surface 82 to create a return current path from electrode terminals 58, through target tissue 52, to return electrode 55, as shown by current flux lines 60 and then removed via transport lumen 57.

Figure 4:
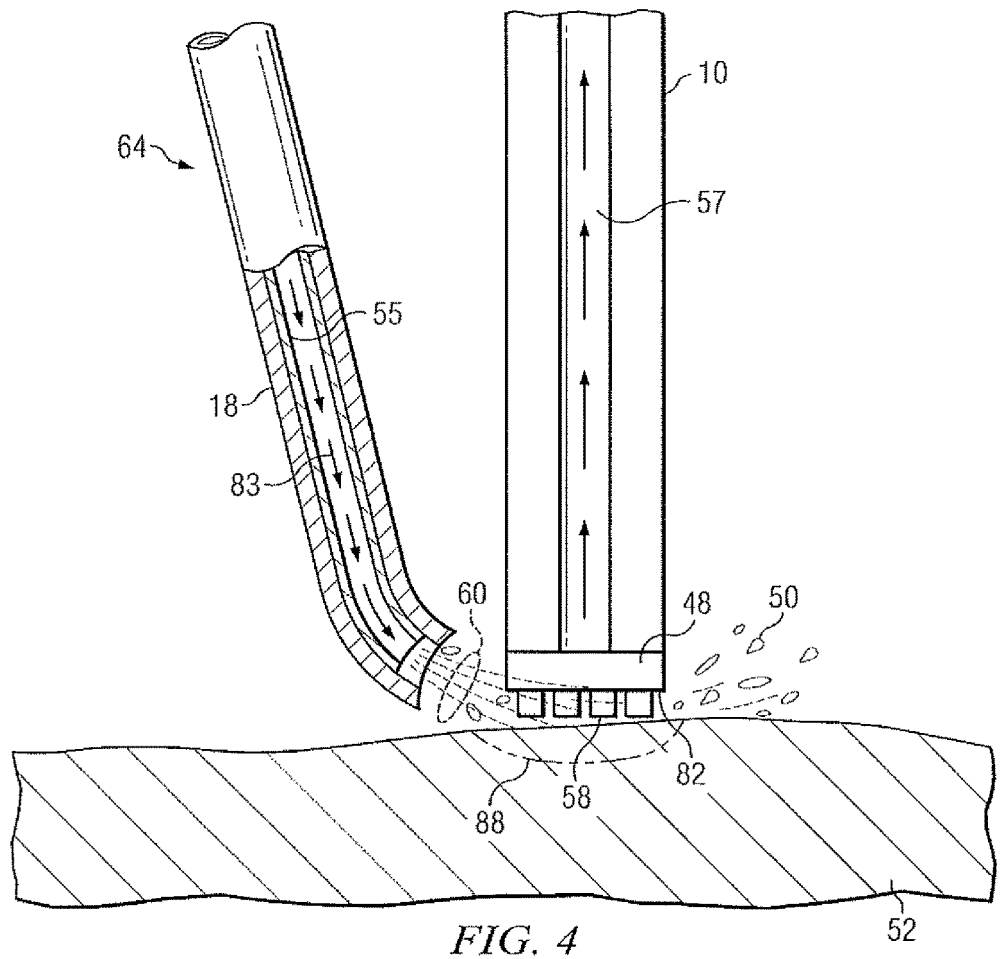
FIG. 4 illustrates an electrosurgical probe and a separate liquid supply instrument.

FIG. 4 illustrates an electrosurgical system 11 further includes a separate liquid supply instrument 64 for supplying electrically conducting fluid 50 between electrode terminals 58 and return electrode 55. Liquid supply instrument 64 comprises an inner tubular member or return electrode 55 surrounded by an electrically insulating jacket 18. Return electrode 55 defines an inner passage 83 for flow of fluid 50. As shown in FIG. 4, the distal portion of instrument 64 is preferably bent so that liquid 50 is discharged at an angle with respect to instrument 64. This allows the surgical team to position liquid supply instrument 64 adjacent electrode surface 82 with the proximal portion of supply instrument 64 oriented at a similar angle to probe 10. Transport lumen 57 may preferably be used in conjunction with a suction pump and controller to remove ablated tissue from a treatment site at a desired flow rate according to operational parameters indicative of conditions at the distal portion of probe 10.

Figure 5:
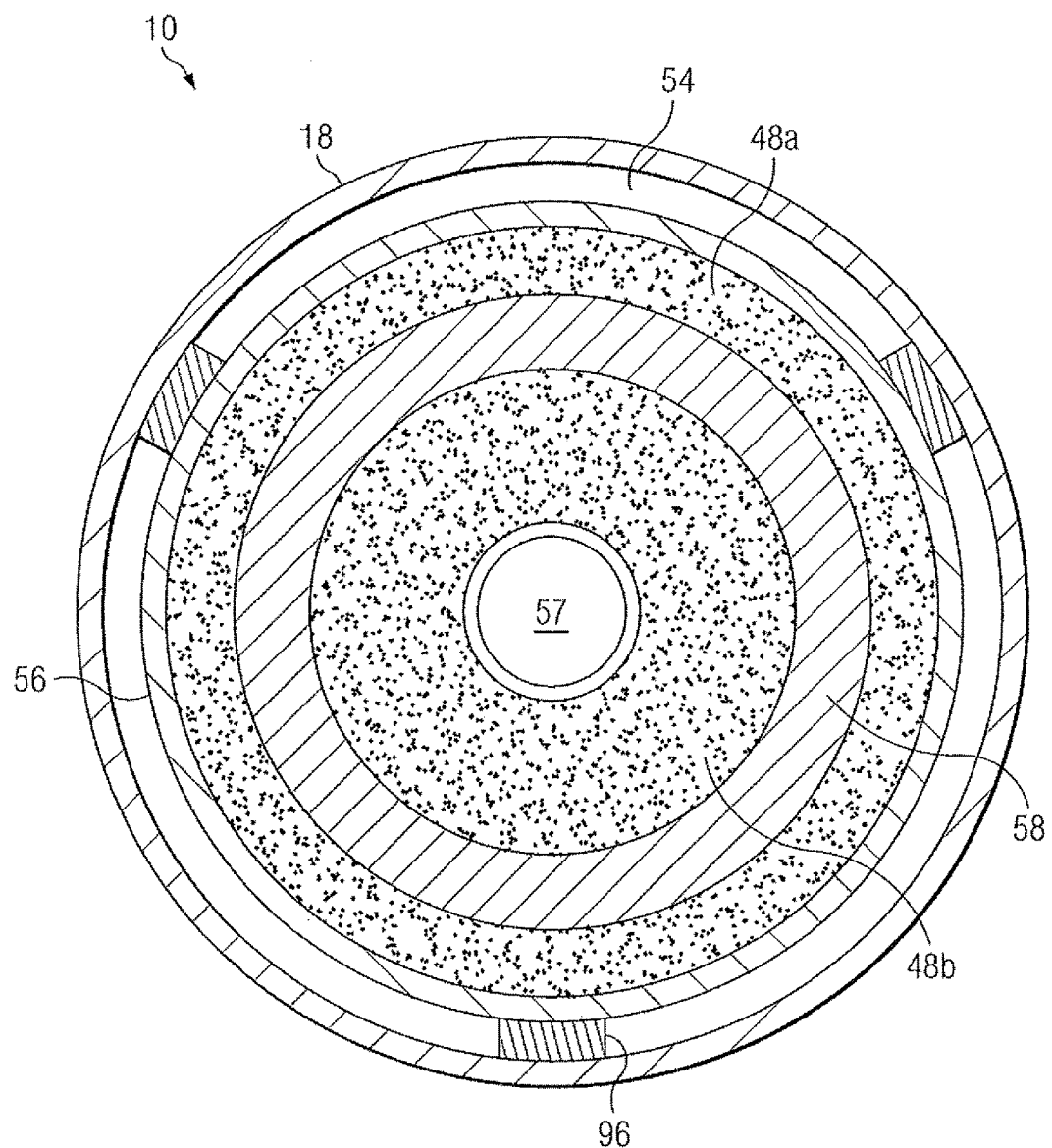
FIG. 5 illustrates the design of a probe including an active electrode with a ring-shaped geometry.

FIG. 5 illustrates another probe 10 comprising a single active electrode 58 having a tubular geometry. As described above, the return electrode may be an outer tubular member 56 and adhesively joins to active electrode support members 48a and 48b. Electrode support members 48a and 48b may be ceramic, glass ceramic or other electrically insulating material which resists carbon or arc tracking. A preferred electrode support member material is alumina. In the example embodiment, alumina forms an inner portion 48b of electrode support member 48 and a hollow tube of alumina forms an outer portion 48a of electrode support member 48. Fluid transport lumen 57 is provided in the interior of inner portion 48b. Tubular or ring-shaped active electrode 58 may be fabricated using shaped cylinder of this metal comprising an electrically conductive metal, such as platinum, tantalum, tungsten, molybdenum, columbium or alloys thereof. An electrically insulating jacket 18 surrounds tubular member 56 and may be spaced from member 56 by a plurality of longitudinal ribs 96 to define an annular gap 54 therebetween (FIG. 5). Annular gap 54 preferably has a width in the range of 0.15 to 4 mm. Ribs 96 can be formed on either jacket 18 or tubular member 56. The distal end of the return electrode 56 is preferably about 0.5 mm to 10 mm and more preferably about 1 to 10 mm from the support surface and will generally depend on the electrical conductivity of the irrigant solution.

The configuration depicted in FIG. 5 may be used with the integral supply means and return electrodes described above. Alternatively, these probe configuration of FIG. 5 may be operated in body cavities already containing an electrically conducting liquid, obviating the need for either an integral supply of said liquid or an electrically insulating sleeve to form a conduit for supply of the electrically conducting liquid 50. Instead, an electrically insulating covering may be applied to substantially all of the return electrode 56 (other than the proximal portion).

Figure 6A:
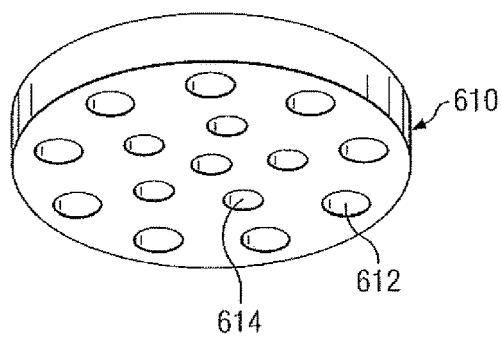
FIGS. 6A-6C illustrate the design of a probe having a screen-type active electrode.
Figure 6B:
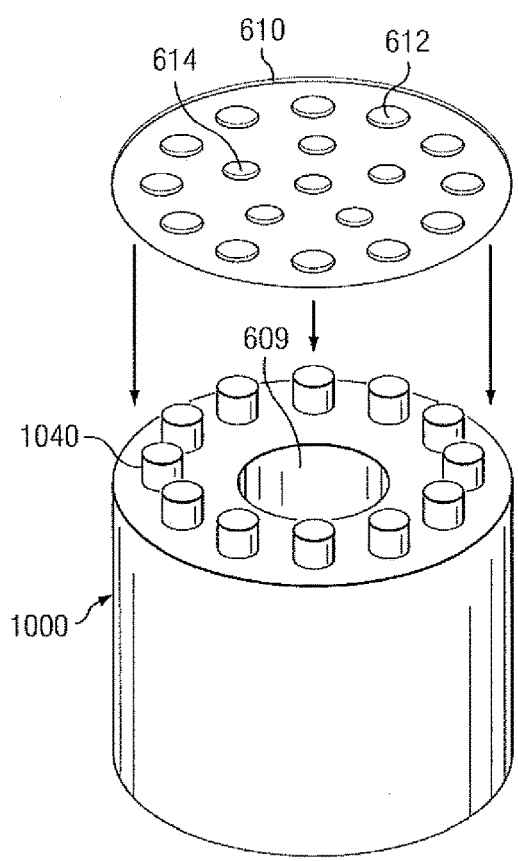
Figure 6C:
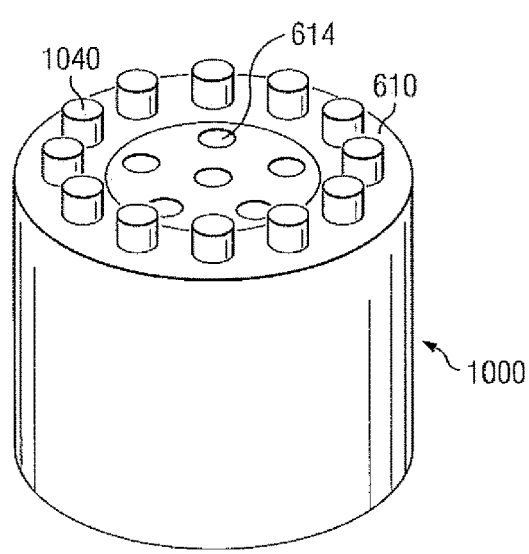

Referring now to FIGS. 6A-6C, an alternative embodiment incorporating a metal screen 610 electrode is illustrated. As shown, metal screen 610 has a plurality of peripheral openings 612 for receiving electrode terminals 1040, and a plurality of inner openings 614 for allowing aspiration of fluid and tissue through opening 609 of the fluid transport lumen. As shown, screen 610 is press fitted over electrode terminals 1040 and then adhered to shaft 1000 of probe 10. In alternate embodiments, metal screen 610 may comprise a mesh-type configuration and may further comprise a variety of conductive metals, such as titanium, tantalum, steel, stainless steel, tungsten, copper, gold or the like.

Figure 7:
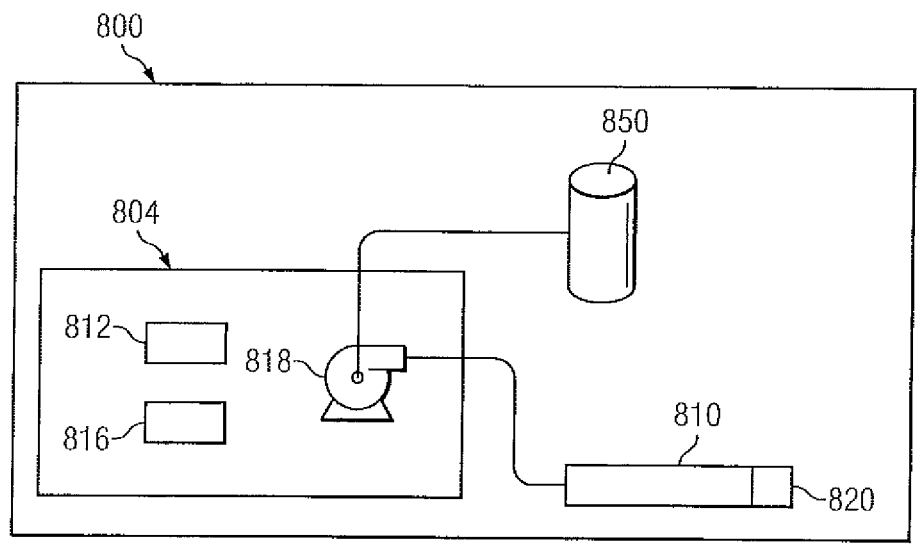
FIG. 7 illustrates a schematic view of an electrosurgical system including a generator, a probe, and a fluid source.

FIG. 7 is a schematic diagram of an electrosurgical system 800 in accordance with one embodiment of the present invention. Electrosurgical system 800 includes a generator 804, an electrosurgical wand 810 coupled to the generator, and a fluid source or supply 850 in fluid communication with the generator 804. As described herein, the generator is operable to automatically identify the type of device 810 when the device is connected to the generator. The generator further determines at least one device specific operational parameter corresponding to the specific type of device. A mode of operation for the generator related to the device specific operational parameter (e.g., an optimal flowrate specific to the device at which to activate the pump) is automatically and dynamically adjusted not only according to the type of device identified, but may also be adjusted according to an expected procedure type and/or a type of target tissue desired to be treated that is typically associated with the particular selected device. The operating parameter status may then be presented to the operator, and the operator then accepts or modifies the device specific operational parameter and carries out the surgical procedure.

Generator 804 may encompass any suitable hardware and software (including but not limited microprocessors and programmable logic controls) necessary to obtain and receive input and to control various outputs such as activating and controlling RF power output, fluid drive component, or perhaps, a suction source. The generator shown in FIG. 7 includes a RF power output 812, a controller 816, and a fluid drive component 818. The fluid drive component 818 may be a pump such as a peristaltic pump or another mechanism to control the flowrate of the liquid from the fluid supply 850 to the wand 810. In an alternative embodiment, the fluid drive component 818 is a controllable valve that restricts flow through the transport line.

Figure 8:
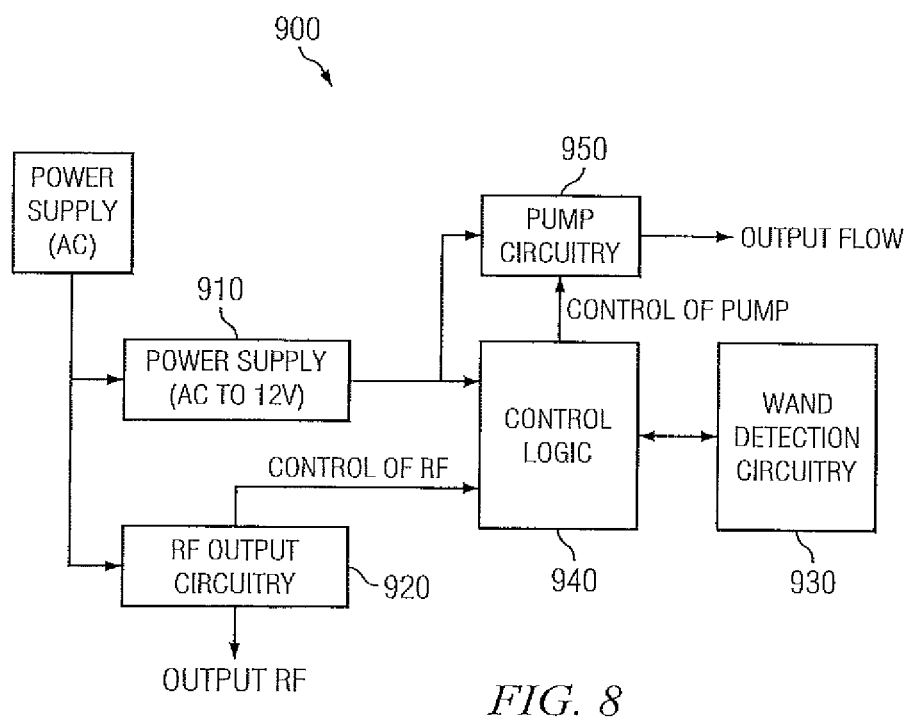
FIG. 8 illustrates a block diagram of an electrosurgical generator.

The individual components or modules of the generator may be configured variously. FIG. 8 illustrates a block diagram of one configuration for a generator in accordance with the present invention. In particular, generator layout 900 comprises a plurality of modules including an AC to DC circuit 910 for converting typical 120 V AC to 12 V DC and a RF output circuit 920 for supplying RF output to an electrosurgical device. A wand type detection circuit 930 for detecting specific types of wands provides input to a control logic circuit 940. Control logic circuitry 940 (or sometimes referred to herein as the "controller") is operable to detect information unique to the type or class of wands. In one embodiment, the wand type is identified based on electrical resistance of the wand (e.g., each type of wand may be designed to have a unique electrical resistance in a wand ID circuit). Although electrical resistance is described as one technique to ID the type of wand, other techniques for identification and recognition are intended to be part of the present invention except where excluded by the appended claims. Indeed, the specific technique for identifying the wand may vary widely. In addition to automatic detection, the operator may manually select the wand type.

FIG. 8 also shows a pump circuit 950 for receiving a signal from the control logic circuit and modifying the output flow to the pump. The modules shown in FIG. 8 are integrated in one generator. However, in other embodiments, the modules and components may be integrated differently or stand alone.

Figure 9:
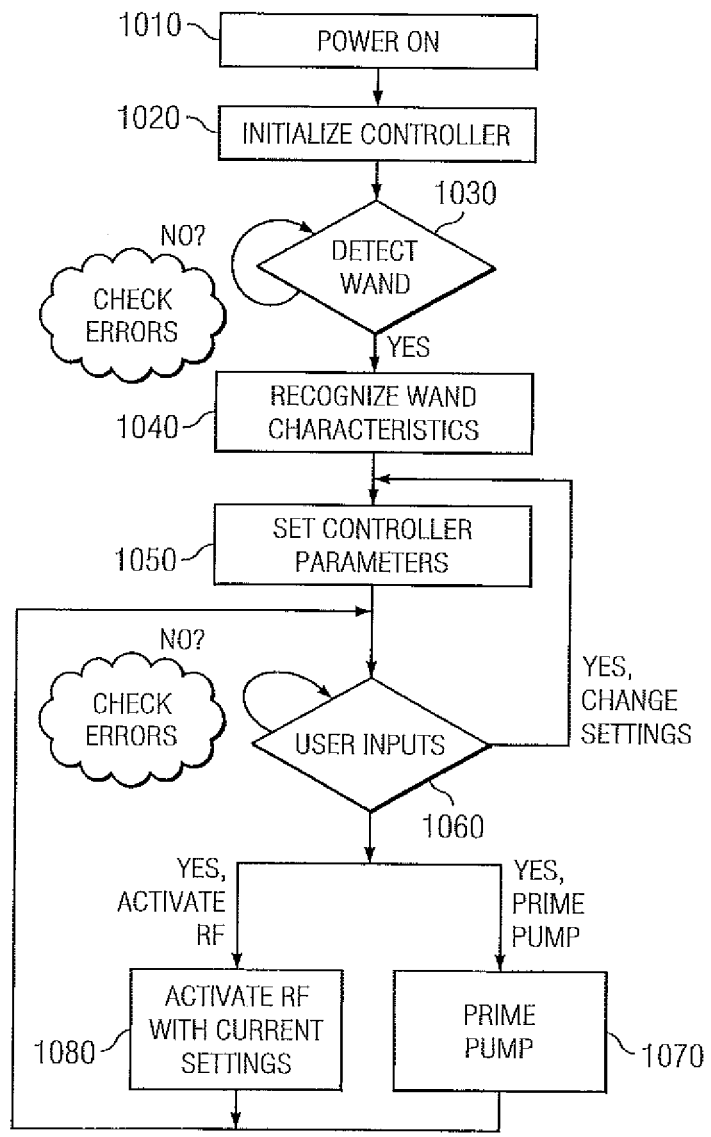
FIG. 9 illustrates a flow chart of the steps of an electrosurgical method of operation in accordance with the present invention.

FIG. 9 illustrates a method of operation in accordance with one embodiment of the present invention. First, controller is powered on 1010 and initialized 1020.

Next, the controller determines whether an electrosurgical device is operably coupled to the generator 1030. If no wand is detected, the controller may indicate the same or indicate an error.

If a wand is detected in step 1030, the controller then identifies the wand type 1040. Identifying the wand type may be performed by comparing the characteristics of the detected wand to a library of characteristics of known wand types. The library or database may be stored in the generator, on removable media, or accessed through an internet or server connection. Alternatively, the wand type may be determined using an algorithm or program.

The generator is adapted to identify a wide variety of types of wands. Preferably, the number of wand types that may be matched includes more than 2 and less than 50 and more preferably, about 2-20 types of wands, and most preferably between 5-10. Each stored wand type shall have associated with it at least one device specific operational parameters. Such device specific operational parameters may be optimized for each device based on analytical, theoretical, and or empirical data.

Once the wand type is identified, the controller sets at least one operational parameter corresponding to the specific wand type 1050. The device specific operational parameters include but are not limited to a) flowrates at which to drive the electrically conductive fluid to through the transport line, b) alarm conditions, c) energy stop conditions, d) count or timer durations, and e) device activation durations. These device specific operational parameters are preferably automatically determined and serve to optimize the procedure and minimize human errors.

Flowrate is one device specific operational parameter in accordance with the present invention. Preferably, although not required, at least three candidate flowrates are set by the controller. Examples include a minimum flowrate, a maximum flowrate, and an initial flowrate. In one embodiment, the flowrate ranges from 5-50 mls per minute and more preferably from 45-65 mls per minute for certain ENT wand procedures (e.g., turbinate reduction) and 10-16 mls per minute for spine surgery procedures (e.g., discectomy). Additionally, the controller may be operable to further modify and optimize the operational flowrates for a specific wand type based on the output energy setting (i.e., voltage settings applicable to ablate or coagulate modes) or based on the voltage level selected by the operator. For example, the controller may be programmed such that detection of a higher voltage level setting would support a higher (or lower) flow rate in one type of device and not another. By way of another example, the controller may be programmed such that operation at certain output energy settings corresponding to one of an ablation or coagulation mode would result in a dynamic adjustment of flow rate in specific devices.

Alarm condition is another device specific operational parameter. Each wand type may include customized alarm conditions. This may include one or more of the following: a) monitoring the output current of the wand and setting the appropriate current-limiting error trigger points, b) monitoring temperature for various internal components inside the RF generator assembly, and c) limiting the total time for which the wand may be operably connected to the RF generator.

Counter or beeper duration is another device specific operational parameter. For wands which are typically used in a time-based procedure, such as a turbinate reduction in which the electrosurgical device is activated for a set period of time to create a lesion, the beeper function in the system may be set for a periodic count duration (e.g., five seconds) such that any time the ablation setting of this wand is activated, the generator will produce an audible tone every count duration to indicate to the user that the wand has been activated for an elapsed period of time. The frequency of the beeper function in the system can be set to a different time interval for each wand type.

Device activation duration is another device specific operational parameter. For wands which are typically used in a time-based procedure such as a turbinate reduction, as described above, or a spinal disc decompression in which the electrosurgical device is activated for a set period of time to limit the ablation inside the disc space, the timer function in the system may be set to allow for the appropriate duration of the RF output from the generator. Non-limiting examples include 20 seconds for turbinate reduction procedures, 10-20 seconds for various percutaneous discectomy procedures, and 40 seconds for open discectomy type of procedures. The device activation duration for which RF can remain active in the system is set to different time intervals for each applicable wand type.

After the candidate operational parameters are set in step 1050, the operator may input or modify the candidate device specific operational parameters. This user input step 1060 allows the operator to accept, increase or decrease the operational parameter (e.g., the flowrate) within the specified range for the type of wand as the doctor desires.

Next, and if applicable, the controller instructs the pump to prime the line 1070. This is necessary to remove air and gas in the line prior to commencing ablation.

Next, step 1080 illustrates activation of RF to ablate or otherwise treat a target tissue using the wand. The method may be repeated as desired and carried out with numerous types of wands.

The above described method is an illustration of one embodiment. Other modifications and variations can be made to the disclosed embodiments without departing from the subject invention. For example, although the controller, power supply, and fluid delivery device have been described above as an integrated assembly, they need not be so integrated. The components may be stand-alone devices and adapted to communicate with one another through input and output ports. Additionally, other uses or applications are possible. Numerous other methods of controlling or characterizing instruments or otherwise treating tissue using electrosurgical probes will be apparent to the skilled artisan. Moreover, the instruments and methods described herein may be utilized in instruments for various regions of the body (e.g., mouth, nasal passageway and other airways, disc, spine, shoulder, knee, etc.) and for other tissue treatment procedures (e.g., discectomy, tonsillectomy, turbinate reduction, chondroplasty, menectomy, etc.). Thus, while the exemplary embodiments have been described in detail, by way of example and for clarity of understanding, a variety of changes, adaptations, and modifications will be obvious to those of skill in the art. Therefore, the scope of the present invention is limited solely by the appended claims.

What is claimed is:
1. An electrosurgical system for treating tissue at a target site during an open procedure comprising:
an electrosurgical device comprising a shaft having a distal end and an active electrode terminal disposed near the distal end, and a return electrode disposed on the device shaft at a location spaced proximally from the active electrode terminal;
a generator comprising:
a high frequency power supply configured to deliver high frequency energy to said active electrode terminal and said return electrode;
a pump configured to pump electrically conductive fluid to the target site and wherein the electrically conductive fluid provides a current path between the active electrode terminal and the return electrode; and
a controller configured to identify a device type of said electrosurgical device when said electrosurgical device is operationally connected to said generator and to automatically determine at least one operational parameter specific to said device type and a selected operating mode, and wherein said at least one operational parameter comprises an ablation candidate flowrate for delivering said electrically conductive fluid when the selected operating mode is an ablation mode, and a coagulation candidate flowrate that is non-zero and lower than the ablation candidate flowrate for delivering electrically conductive fluid when a coagulation operating mode is selected; wherein both candidate flowrates are configured to control the current path between the return electrode and active electrode terminal and thereby limit heating of the tissue; and
wherein the electrosurgical device and the generator are configured to volumetrically remove tissue in a non-thermal manner and thereby ablate the tissue when the ablation mode is selected, and wherein the electrosurgical device and the generator are configured to provide hemostasis to the tissue when coagulation mode is selected.

2. The system of claim 1 wherein the controller is configured to determine at least 3 different candidate flowrates for delivering electrically conductive fluid to the target site based on the device type and selected operating mode.

3. The system of claim 1 wherein said controller is configured to determine a minimum and maximum candidate flowrate for delivering electrically conductive fluid to the target site based on the device type and the operating mode.

4. The system of claim 3 wherein said minimum candidate flowrate is 8 milliliters per minute, and said maximum candidate flowrate is 65 milliliters per minute.

5. The system of claim 1 wherein the controller comprises a library of preselected candidate flowrates corresponding to a plurality of types of devices and operating modes.

6. The system of claim 1 wherein said controller is configured to identify said device type based on an electrical resistance associated with the device when the device is connected to the generator.

7. The system of claim 1 wherein said at least one operational parameter further comprises one or more of the following: alarm condition, energy stop condition, count duration, and device activation duration.

8. The system of claim 7 wherein said at least one operational parameter comprises the alarm condition and said controller is configured to produce an alarm signal when said alarm condition is met.

9. The system of claim 7 wherein said at least one operational parameter comprises the energy stop condition and said stop condition includes at least one of the following: a) output current of the device, and b) total time that the device is connected to the generator.

10. The system of claim 7 wherein said at least one operational parameter comprises a periodic count duration based on the device type and wherein the controller indicates the completion of the count duration.

11. The system of claim 10 wherein the generator is configured to produce an audible tone.

12. The system of claim 7 wherein said at least one operational parameter comprises the device activation duration based on the device type and the controller is configured to stop delivery of high frequency energy to the device upon completion of the device activation duration.

13. The system of claim 12 wherein said device activation duration is equal to or greater than 20 seconds and less than or equal to 40 seconds.

14. The system of claim 1 wherein the pump is a peristaltic pump.

15. The system of claim 14 wherein the electrosurgical device comprises an integrated fluid delivery channel.

16. The system of claim 15 further comprising an electrically conductive fluid supply reservoir fluidly coupled to the integrated fluid delivery channel.

17. The system of claim 16 further comprising a foot pedal coupled to the generator, and wherein the generator is configured to activate delivery of high frequency energy to the active electrode terminal responsive to activation of the foot pedal.

18. The system of claim 1 wherein both candidate flowrates are configured to flow over both the active and return electrodes followed by flowing away from the target site through an opening of the nose or mouth near the target tissue.

19. The system of claim 1, wherein the generator is configured to produce high frequency energy sufficient to vaporize a portion of the electrically conductive fluid and form an ionized gas to ablate the tissue when the ablation mode is selected, and wherein the ablation candidate flow rate delivers the electrically conductive fluid at a rate that improves the efficiency of ionized gas formation and tissue ablation.

20. The system of claim 1 wherein the ablation candidate flowrate is lower than the coagulation candidate flowrate.

21. The system of claim 1, wherein the controller is further configured to activate the pump based on the candidate flow rate and to adjust an operational flow rate of the conductive fluid based on both the device type and the selected operational mode.

22. The system of claim 1, wherein the controller is further configured so that the adjustment to the operational flow rate also based on voltage level selected within each operational mode, so that detection of a higher voltage level causes a selected change in operational flow rate in a first device type but not in a second device type.

23. An electrosurgical generator comprising:
a high frequency power supply configured to deliver high frequency energy to an active electrode terminal and a return electrode of an electrosurgical device, the high frequency energy sufficient to form an ionized gas adjacent the active electrode terminal;
a means for controlling delivery of electrically conductive fluid to a target site adjacent the active electrode terminal; and
a controller configured to identify a device type of said electrosurgical device when said electrosurgical device is operationally connected to said generator, and said controller configured to automatically determine at least one operational parameter specific to said device type and operating mode of the high frequency power supply, and wherein said at least one operational parameter comprises at least one candidate flowrate, comprising an ablation candidate flowrate for delivering said electrically conductive fluid at a rate that is configured to form an electrical path between the active electrode terminal and the return electrode, cover a portion of the active electrode terminal sufficient for electrically conductive fluid vaporization and limit heating of adjacent tissue when sufficient high frequency energy is supplied; and a coagulation candidate flowrate that is non-zero for delivering said electrically conductive fluid at a rate lower than the ablation candidate flowrate and configured to control the current path between the active electrode terminal and return electrode so as to increase heating of the adjacent tissue, when sufficient high frequency energy is supplied; and wherein the controller is further configured to activate the means for controlling delivery based on the candidate flow rate and to adjust an operational flow rate of the conductive fluid based on both the device type and the operating mode.

24. An electrosurgical generator comprising:

a high frequency power supply configured to deliver high frequency energy to an active electrode terminal and a return electrode of an electrosurgical device;

a pump configured to deliver electrically conductive fluid to a target site and wherein the electrically conductive fluid provides a current path between the active electrode terminal and the return electrode; and a controller configured to identify a device type of said electrosurgical device when said electrosurgical device is operationally connected to said generator, and the controller is configured to automatically determine at least one operational parameter specific to said device type and operating mode selected;

wherein the electrosurgical generator is configured to produce high frequency energy sufficient to vaporize a portion of the electrically conductive fluid and form an ionized gas to ablate the tissue when a first operating mode is selected, and wherein the pump activates the electrically conductive fluid at a first fluid flow rate that is configured to control the current path between the return electrode and active electrode terminal and thereby limit heating of tissue adjacent the target site, and wherein the pump adjusts the first fluid rate during operation based on the device type and the first operating mode; and wherein the electrosurgical generator is configured to produce high frequency energy sufficient to cause hemostasis of the tissue when a second operating mode is selected, and wherein the pump delivers the electrically conductive fluid at a second fluid flow rate lower than when in the first operating mode, and at a non-zero rate that is configured to control the current path though the tissue adjacent the target site, and thereby increase hemostasis of the adjacent tissue relative to the first operating mode; and wherein the pump adjusts the second rate during operation based on the device type and the second operating mode.

25. The generator of claim 24 wherein the at least one operational parameter comprises a plurality of operational parameters.

26. The generator of claim 25 wherein the plurality of operational parameters comprises one or more of the following: candidate flowrate, alarm condition, energy stop condition, count duration, and device activation duration.

27. The generator of claim 24 wherein the at least one operational parameter specific to the device type is further specific to a procedure type.

28. The generator of claim 24 wherein the at least one operational parameter specific to the device type is further specific to a target tissue type.

29. A system for treating tissue in an open procedure comprising:

an electrosurgical wand comprising a shaft having a distal end, an active electrode terminal disposed near the distal end, and a return electrode disposed on the shaft at a location spaced proximally from the active electrode terminal;

an electrosurgical control system in the form of an integrated unit, the electrosurgical control system comprising:

a high frequency power supply electrically coupled to the active electrode and the return electrode, the high frequency power supply configured to deliver high frequency energy to the active electrode terminal and said return electrode;

a peristaltic pump configured to pump electrically conductive fluid to a surgical site adjacent the return electrode, the electrically conductive fluid configured to provide an electrical current path between the active electrode terminal and the return electrode; and a controller configured to identify a device type of the electrosurgical wand when the electrosurgical wand is operationally connected to the electrosurgical device, and the controller configured to automatically determine at least one operational parameter specific to said device type and a selected operating mode, and wherein said at least one operational parameter comprises an ablation candidate flowrate for delivering said electrically conductive fluid when the selected operating mode is an ablation mode, and a coagulation candidate flowrate that is non-zero and lower than the ablation candidate flowrate for delivering electrically conductive fluid when a coagulation operating mode is selected;

the electrosurgical wand and electrosurgical device are configured to volumetrically remove tissue in a non-thermal manner and thereby ablate the tissue when the ablation mode is selected, and wherein the electrosurgical device and the generator are configured to provide hemostasis to the tissue when coagulation mode is selected; and wherein both the candidate flowrates control the current path from the return electrode to the active electrode terminal so as to control the current path through the tissue and thereby heating of the tissue.

* * * * *